United States Patent
Koizumi et al.

(10) Patent No.: US 11,433,090 B2
(45) Date of Patent: Sep. 6, 2022

(54) MTOR-INHIBITOR-CONTAINING MEDICINE FOR TREATING OR PREVENTING OPHTHALMIC SYMPTOMS, DISORDERS, OR DISEASES, AND APPLICATION THEREOF

(71) Applicant: The Doshisha, Kyoto (JP)

(72) Inventors: Noriko Koizumi, Kyoto (JP); Naoki Okumura, Kyoto (JP)

(73) Assignee: The Doshisha, Kyoto (JP)

( * ) Notice: Subject to any disclaimer, the term of this patent is extended or adjusted under 35 U.S.C. 154(b) by 106 days.

(21) Appl. No.: 16/621,881

(22) PCT Filed: Jun. 15, 2018

(86) PCT No.: PCT/JP2018/022942
§ 371 (c)(1),
(2) Date: Dec. 12, 2019

(87) PCT Pub. No.: WO2018/230711
PCT Pub. Date: Dec. 20, 2018

(65) Prior Publication Data
US 2020/0113925 A1   Apr. 16, 2020

(30) Foreign Application Priority Data

Jun. 16, 2017 (JP) .............................. JP2017-118619

(51) Int. Cl.
| A61P 27/02 | (2006.01) |
| A61K 31/711 | (2006.01) |
| A61K 31/7105 | (2006.01) |
| A61K 31/436 | (2006.01) |
| C12Q 1/68 | (2018.01) |
| A61K 45/06 | (2006.01) |

(52) U.S. Cl.
CPC .......... *A61K 31/711* (2013.01); *A61K 31/436* (2013.01); *A61K 31/7105* (2013.01); *A61P 27/02* (2018.01); *A61K 45/06* (2013.01)

(58) Field of Classification Search
None
See application file for complete search history.

(56) References Cited

U.S. PATENT DOCUMENTS

| 5,387,589 | A | 2/1995 | Kulkarni |
| 7,563,906 | B2 | 7/2009 | Hagihara et al. |
| 8,227,480 | B2 | 7/2012 | Hagihara et al. |
| 8,426,406 | B2 | 4/2013 | Kato et al. |
| 8,663,639 | B2 | 3/2014 | Dor et al. |
| 8,664,221 | B2 | 3/2014 | Kato et al. |
| 8,802,869 | B2 | 8/2014 | Kudou et al. |
| 9,029,572 | B2 | 5/2015 | Kudou et al. |
| 9,650,351 | B2 | 5/2017 | Nakajima et al. |
| 9,676,703 | B2 | 6/2017 | Kudou et al. |
| 10,149,908 | B2 | 12/2018 | Endo |
| 10,189,796 | B2 | 1/2019 | Kawashima et al. |
| 2005/0025810 | A1 | 2/2005 | Peyman |
| 2005/0282792 | A1 | 12/2005 | Andres |
| 2006/0122282 | A1 | 6/2006 | Leonard |
| 2006/0154235 | A1 | 7/2006 | Ochiya et al. |
| 2007/0105761 | A1 | 5/2007 | Chappell et al. |
| 2009/0022807 | A1 | 1/2009 | Li |
| 2009/0111807 | A1 | 4/2009 | Matsuda et al. |
| 2009/0298826 | A1 | 12/2009 | Matsuda et al. |
| 2009/0298827 | A1 | 12/2009 | Matsuda et al. |
| 2010/0056504 | A1 | 3/2010 | Matsuda et al. |
| 2010/0209505 | A1 | 8/2010 | Rossignol et al. |
| 2010/0227879 | A1 | 9/2010 | Mudumba et al. |
| 2011/0263600 | A1 | 10/2011 | Matsuda et al. |
| 2011/0275620 | A1 | 11/2011 | Matsuda et al. |
| 2011/0275632 | A1 | 11/2011 | Matsuda et al. |
| 2011/0300195 | A1* | 12/2011 | Mitra .................. A61K 31/355 424/400 |
| 2012/0045435 | A1 | 2/2012 | Deisher |
| 2012/0190705 | A1 | 7/2012 | Wen et al. |
| 2014/0018348 | A1 | 1/2014 | Javitt |
| 2014/0370007 | A1 | 12/2014 | McCabe et al. |
| 2015/0044178 | A1 | 2/2015 | Kinoshita et al. |
| 2015/0157687 | A1 | 6/2015 | Mitra et al. |

(Continued)

FOREIGN PATENT DOCUMENTS

| EP | 3064222 A1 | 9/2016 |
| EP | 3381472 A1 | 10/2018 |

(Continued)

OTHER PUBLICATIONS

Altschul et al., Basic local alignment search tool, J. Mol. Biol., 215(3):403-10 (Oct. 1990).

Engler et al., Unfolded protein response in fuchs endothelial corneal dystrophy: a unifying pathogenic pathway?, Am. J. Opthalmol., 149(2):194-202 (Feb. 2010).

European Patent Application No. 18817351.2, Extended European Search Report, dated Jul. 6, 2020.

(Continued)

*Primary Examiner* — Sean McGarry

(74) *Attorney, Agent, or Firm* — Marshall, Gerstein & Borun LLP

(57) ABSTRACT

The present invention provides a medicine and a method for preventing or treating ophthalmic symptoms, disorders, or diseases. The present invention provides an mTOR-inhibitor-containing composition for preventing or treating ophthalmic symptoms, disorders, or diseases. In some of the embodiments of the present invention, this composition is capable of treating or preventing corneal endothelial symptoms, disorders, or diseases; in particular, corneal endothelial symptoms, disorders, or diseases that are attributed to overexpression of the transforming growth factor-β (TGF-β) signal and/or extracellular matrix (ECM).

16 Claims, 21 Drawing Sheets

Specification includes a Sequence Listing.

(56) References Cited

U.S. PATENT DOCUMENTS

| | | |
|---|---|---|
| 2016/0120847 A1 | 5/2016 | Malhotra et al. |
| 2016/0158210 A1 | 6/2016 | Koizumi et al. |
| 2016/0296505 A1 | 10/2016 | Koizumi et al. |
| 2017/0290821 A1 | 10/2017 | Kawaoka et al. |
| 2018/0185489 A1 | 7/2018 | Miyazaki et al. |
| 2018/0369220 A1 | 12/2018 | Koizumi et al. |
| 2020/0113925 A1 | 4/2020 | Koizumi et al. |

FOREIGN PATENT DOCUMENTS

| | | |
|---|---|---|
| EP | 3395364 A1 | 10/2018 |
| JP | 2001-097865 A | 4/2001 |
| JP | 2004-2352 A | 1/2004 |
| JP | 2004-107335 A | 4/2004 |
| JP | 2004-137267 A | 5/2004 |
| JP | 2004-254509 A | 9/2004 |
| JP | 2004-256524 A | 9/2004 |
| JP | 2004-331501 A | 11/2004 |
| JP | 2005-41866 A | 2/2005 |
| JP | 2005-47909 A | 2/2005 |
| JP | 2005-336173 A | 12/2005 |
| JP | 2005-336174 A | 12/2005 |
| JP | 2006-117653 A | 5/2006 |
| JP | 2006-117654 A | 5/2006 |
| JP | 2006-151968 A | 6/2006 |
| JP | 2006-254896 A | 9/2006 |
| JP | 2006-257080 A | 9/2006 |
| JP | 2007-8816 A | 1/2007 |
| JP | 2007-15928 A | 1/2007 |
| JP | 2007-77049 A | 3/2007 |
| JP | 2007-230993 A | 9/2007 |
| JP | 2007-291091 A | 11/2007 |
| JP | 2007-297283 A | 11/2007 |
| JP | 2008-74829 A | 4/2008 |
| JP | 2008-143889 A | 6/2008 |
| JP | 2008-143890 A | 6/2008 |
| JP | 2008-143891 A | 6/2008 |
| JP | 2008-143913 A | 6/2008 |
| JP | 4-134093 B2 | 8/2008 |
| JP | 2008-255112 A | 10/2008 |
| JP | 2008-266295 A | 11/2008 |
| JP | 2008-266323 A | 11/2008 |
| JP | 2009-007344 A | 1/2009 |
| JP | 2009-29828 A | 2/2009 |
| JP | 2009-84273 A | 4/2009 |
| JP | 2009-84274 A | 4/2009 |
| JP | 2009-143940 A | 7/2009 |
| JP | 2009-538879 A | 11/2009 |
| JP | 2009-298775 A | 12/2009 |
| JP | 2010-77119 A | 4/2010 |
| JP | 2010-90117 A | 4/2010 |
| JP | 4817020 B2 | 11/2011 |
| JP | 4825636 B2 | 11/2011 |
| JP | 2012-067097 A | 4/2012 |
| JP | 2012-180345 A | 9/2012 |
| JP | 5054996 B2 | 10/2012 |
| JP | 2013-509179 A | 3/2013 |
| JP | 2013-515018 A | 5/2013 |
| JP | 2013-518812 A | 5/2013 |
| JP | 2013-166752 A | 8/2013 |
| JP | 2014-19650 A | 2/2014 |
| JP | 2014-31369 A | 2/2014 |
| JP | 2014-139161 A | 7/2014 |
| JP | 2014-196268 A | 10/2014 |
| JP | 2014-208611 A | 11/2014 |
| JP | 5635743 B2 | 12/2014 |
| JP | 2015-7122 A | 1/2015 |
| JP | 2015-57381 A | 3/2015 |
| JP | 2015-147762 A | 8/2015 |
| JP | 2015-147763 A | 8/2015 |
| JP | 2016-27060 A | 2/2016 |
| JP | 2016-216425 A | 12/2016 |
| JP | 2017-14209 A | 1/2017 |
| JP | 2017-14269 A | 1/2017 |
| JP | 2017-31177 A | 2/2017 |
| JP | 2017-43614 A | 3/2017 |
| JP | 2017-186375 A | 10/2017 |
| WO | WO-01/58438 | 8/2001 |
| WO | WO-03/011276 A1 | 2/2003 |
| WO | WO-2004/069822 A1 | 8/2004 |
| WO | WO-2005/007161 A1 | 1/2005 |
| WO | WO-2005/035506 A1 | 4/2005 |
| WO | WO-2005/102331 A1 | 11/2005 |
| WO | WO-2007/032556 A1 | 3/2007 |
| WO | WO-2007/056457 A2 | 5/2007 |
| WO | WO-2007/101005 | 9/2007 |
| WO | WO-2007/105766 A1 | 9/2007 |
| WO | WO-2007/142323 A1 | 12/2007 |
| WO | WO-2008/025532 | 3/2008 |
| WO | WO-2008/059865 A1 | 5/2008 |
| WO | WO-2008/059866 A1 | 5/2008 |
| WO | WO-2008/059867 A1 | 5/2008 |
| WO | WO-2008/093674 A1 | 8/2008 |
| WO | WO-2008/111632 A1 | 9/2008 |
| WO | WO-2008/119500 A1 | 10/2008 |
| WO | WO-2008/146871 A1 | 12/2008 |
| WO | WO-2009/035067 A1 | 3/2009 |
| WO | WO-2009/035068 A1 | 3/2009 |
| WO | WO-2009/139361 A1 | 11/2009 |
| WO | WO-2010/029986 A1 | 3/2010 |
| WO | WO-2010/064207 A2 | 6/2010 |
| WO | WO-2010/129622 A1 | 11/2010 |
| WO | WO-2011/053257 A2 | 5/2011 |
| WO | WO-2011/098578 A2 | 8/2011 |
| WO | WO-2011/129371 A1 | 10/2011 |
| WO | WO-2012/108455 A1 | 8/2012 |
| WO | WO-2013/086236 A2 | 6/2013 |
| WO | WO-2013/100208 A1 | 7/2013 |
| WO | WO-2014/010654 A2 | 1/2014 |
| WO | WO-2014/098046 A1 | 6/2014 |
| WO | WO-2014/117117 | 7/2014 |
| WO | WO-2014/148574 A1 | 9/2014 |
| WO | WO-2015/015654 A1 | 2/2015 |
| WO | WO-2015/015655 A1 | 2/2015 |
| WO | WO-2015/020204 A1 | 2/2015 |
| WO | WO-2015/064768 A1 | 5/2015 |
| WO | WO-2015/105134 A1 | 7/2015 |
| WO | WO-2015/105135 A1 | 7/2015 |
| WO | WO-2015/105144 A1 | 7/2015 |
| WO | WO-2015/168523 | 11/2015 |
| WO | WO-2015/169944 | 11/2015 |
| WO | WO-2016/047592 A1 | 3/2016 |
| WO | WO-2016/187718 | 12/2016 |
| WO | WO-2017/002941 A1 | 1/2017 |
| WO | WO-2014/208709 | 2/2017 |
| WO | WO-2017/034006 A1 | 3/2017 |
| WO | WO-2017/110093 A1 | 6/2017 |
| WO | WO-2017/110094 A1 | 6/2017 |
| WO | WO-2018/230711 A1 | 12/2018 |

OTHER PUBLICATIONS

European Patent Application No. 18817847.9, Extended European Search Report, dated Feb. 12, 2021.

International Application No. PCT/JP2018/022944, International Search Report, dated Aug. 28, 2018.

Minamiyama et al., Effect of TGF-β inhibitor on apoptosis of the corneal endothelial cells of Fuchs' endothelial corneal dystrophy, Annual Meeting of Japan Cornea Conference 2014 [Abstract Only].

NCBI Reference Sequence: NM_001128128.2, *Homo sapiens* zinc finger E-box binding homeobox 1 (ZEB1), transcript variant 1, mRNA, Dec. 4, 2019.

NCBI Reference Sequence: NM_001180305.1, *Saccharomyces cerevisiae* S288C hexose transporter HXT15 (HXT15), partial mRNA, Nov. 1, 2019.

NCBI Reference Sequence: NM_001193376.2, *Homo sapiens* telomerase reverse transcriptase (TERT), transcript variant 2, mRNA, Dec. 10, 2019.

NCBI Reference Sequence: NM_005985.4, *Homo sapiens* snail family transcriptional repressor 1 (SNAI1), mRNA, Dec. 10, 2019.

NCBI Reference Sequence: NP_001121600.1, zinc finger E-box-binding homeobox 1 isoform a [*Homo sapiens*], Dec. 4, 2019.

(56) References Cited

OTHER PUBLICATIONS

NCBI Reference Sequence: NP_005976.2, zinc finger protein SNAI1 [*Homo sapiens*], Dec. 10, 2019.
Needleman et al., A general method applicable to the search for similarities in the amino acid sequence of two proteins, J. Mol. Biol., 48(3):443*53 (Mar. 1970).
Okumura et al., Involvement of ZEB1 and Snail1 in excessive production of extracellular matrix in Fuchs endothelial corneal dystrophy, Laboratory Investigation, 95:1291-304 (2015).
Pearson et al., Improved tools for biological sequence comparison, Proc. Natl. Acad. Sci. USA, 85(8):2444-8 (Apr. 1988).
Smith et al., Identification of common molecular subsequences, J. Mol. Biol., 147(1):195-7 (Mar. 1981).
Sundahl et al., Selective glucocorticoid receptor modulation: New directions with non-steroidal scaffolds, Pharmacol. Ther., 152:28-41 (Aug. 2015).
Tonomura et al., Involvement of caspase 7 in the excessive production of extracellular matrix in Fucs endothelial corneal dystrophy, Database Accession No. EMB-629938975, Investigative Ophthalmology and Visual Science 20190701 Association for Research in Vision and Ophthalmology Inc. NLP, vol. 60, No. 9 (Jul. 1, 2019). [ABSTRACT].
Van Horn et al., Regenerative capacity of the corneal endothelium in rabbit and cat, Invest. Ophthalmol. Vis. Sci., 16(7):597-613 (Jul. 1977).
Wigler et al., DNA-mediated transfer of the adenine phosphoribosyltransferase locus into mammalian cells, Proc. Natl. Acad. Sci. USA, 76(3):1373-6 (Mar. 1979).
Wikipedia entry, "Phases of clinical research", published Apr. 17, 2017.
Laura Frost et al., "Autophagy in the eye: Implications for ocular cell health", Experimental Eye Research, 124:56-66 (2014).
Sanaz Gidfar et al., "Rapamycin Prolongs the Survival of Corneal Epithelial Cells in Culture", Scientific Reports, vol. 7, No. 1 (Jan. 5, 2017) Abstract.
Schenone et al., ATP-Competitive Inhibitors of mTOR: An update, Curr. Med. Chem., 18:2995-3014 (2011).
Sanjabi et al., Anti-inflammatory and pro-inflammatory roles of TGF-beta, IL-10, and IL-22 in immunity and autoimmunity, Curr. Opin. Pharmacol., 9(4):447-53 (2009).
Richards, Ophthalmic Products, IN: Winfield et al. (eds.), Pharmaceutical Practice, Churchill Livingstone, pp. 264-265 (2004).
Russian Patent Application No. 2020101227/04, Office Action and Search Report, dated Oct. 14, 2021.
Azizi et al., p53-regulated increase in oxidative-stress-induced apoptosis in Fuchs endothelial corneal dystrophy: a native tissue model, Invest. Ophthalmol. Vis. Sci., 52(13):9291-7 (Dec. 2011).
Border et al., Transforming growth factor-beta in disease: the dark side of tissue repair, J. Clin. Invest., 90(1):1 -7 (Jul. 1992).
Feng et al., Specificity and versatility in tgf-beta signaling through Smads, Annu. Rev. Cell Dev. Biol., 21:659-93 (2005).
Goc et al., TGFß- and bleomycin-induced extracellular matrix synthesis is mediated through Akt and mammalian target of rapamycin (mTOR), J. Cell Physiol., 226(11):3004-13 (Nov. 2011).
International Application No. PCT/JP2018/022942, International Search Report, dated Jul. 31, 2018.
Jun et al., An alpha 2 collagen VIII transgenic knock-in mouse model of Fuchs endothelial corneal dystrophy shows early endothelial cell unfolded protein response and apoptosis, Hum. Mol. Genet., 21(2):384-93 (Jan. 2012).
Kelliher et al., A cellular model for the investigation of Fuchs' endothelial corneal dystrophy, Exp. Eye Res., 93(6):880-8 (Dec. 2011).
Kikuchi et al., Site-specific cleavage of natural mRNA sequences by newly designed hairpin catalytic RNAs, Nucleic Acids Res., 19(24):6751-5 (Dec. 1991).
Koizumi et al., Cleavage of specific sites of RNA by designed ribozymes, FEBS Lett., 239(2):285-8 (Nov. 1988).
Koizumi et al., Construction of a series of several self-cleaving RNA duplexes using synthetic 21-mers, FEBS Lett., 228(2):228-30 (Feb. 1988).
Koizumi et al., Design of RNA enzymes distinguishing a single base mutation in RNA, Nucleic Acids Res., 17(17):7059-71 (Sep. 1989).
Leask et al., TGF-beta signaling and the fibrotic response, Faseb J., 18(7):816-27 (May 2004).
Margadant et al., Integrin-TGF-beta crosstalk in fibrosis, cancer and wound healing, EMBO Rep., 11(2):97-105 (Feb. 2010).
Massague, TGF-beta signal transduction, Annu. Rev. Biochem., 67:753-91 (1998).
Minakuchi et al., Atelocollagen-mediated synthetic small interfering RNA delivery for effective gene silencing in vitro and in vivo, Nucleic Acids Res., 32(13):e109 (Jul. 2004).
Ochiya et al., Biomaterials for gene delivery: atelocollagen-mediated controlled release of molecular medicines, Curr. Gene Ther., 1(1):31-52 (May 2001).
Shin et al., Rapamycin reduces reactive oxygen species in cultured human corneal endothelial cells, Curr. Eye Res., 36(12):1116-22 (Dec. 2011).
Takeshita et al., Efficient delivery of small interfering RNA to bone-metastatic tumors by using atelocollagen in vivo, Proc. Natl. Acad. Sci. USA, 102(34):12177-82 (Aug. 2005).
Vilar et al., Signal processing in the TGF-beta superfamily ligand-receptor network, PLoS Comput. Biol., 2(1):e3 (Jan. 2006).
Zaniolo et al., Culture of human corneal endothelial cells isolated from corneas with Fuchs endothelial corneal dystrophy, Exp. Eye Res., 94(1):22-31 (Jan. 2012).
"Can Fuchs' dystrophy be prevented?", downloaded from the Internet at: <https://www.topdoctors.co.uk/medical-dictionary/fuchs-dystrophy-treatment>, 2022.
"Fuchs' Corneal Dystrophy: 7 Things You Should Know", downloaded from the Internet at: <https://www.allaboutvision.com/conditions/fuchs-corneal-dystrophy.htm>, published Mar. 2019.
Buerke et al., Intramural delivery of Sirolimus prevents vascular remodeling following balloon injury, Biochim. Biophys. Acta, 1774(1):5-15 (2007).
McLaren et al., Objective assessment of the corneal endothelium in Fuchs' endothelial dystrophy, Invest. Ophthalmol. Vis. Sci., 55(2):1184-90 (2014).
Moore et al., An objective assessment of the variability in number of drops per bottle of glaucoma medication, BMC Ophthalmol., 17(1):78 (2017).
Shin et al., Rapamycin reduces reactive oxygen species in cultured human corneal endothelial cells, Curr. Eye Res., 36(12):1116-22 (Oct. 14, 2011).
Zhang et al., Rapamycin attenuates endothelial apoptosis induced by low shear stress via mTOR and sestrin1 related redox regulation, Mediators Inflamm. 2014:769608 (2014).

* cited by examiner

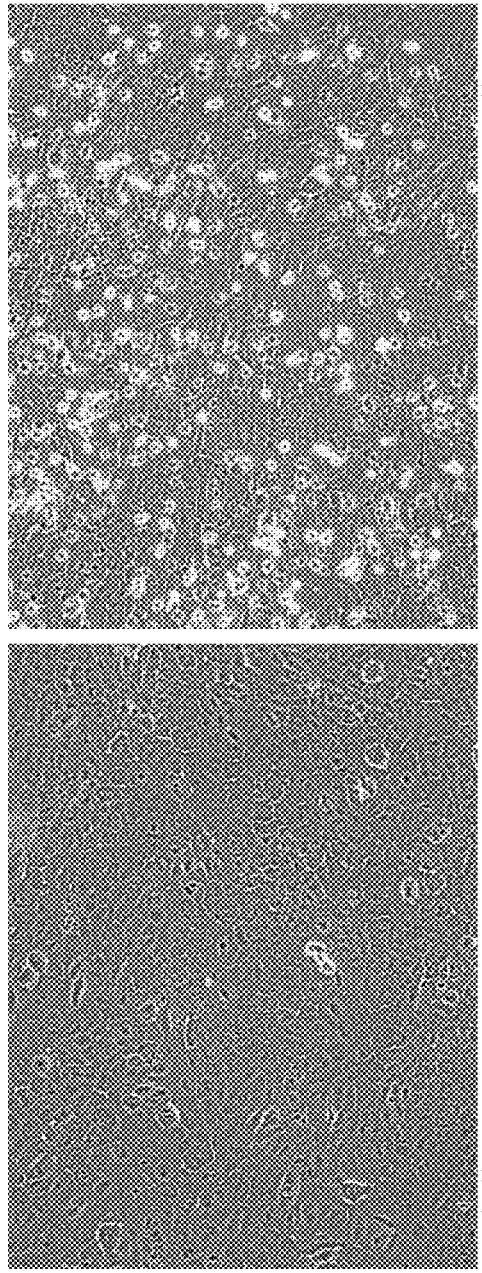
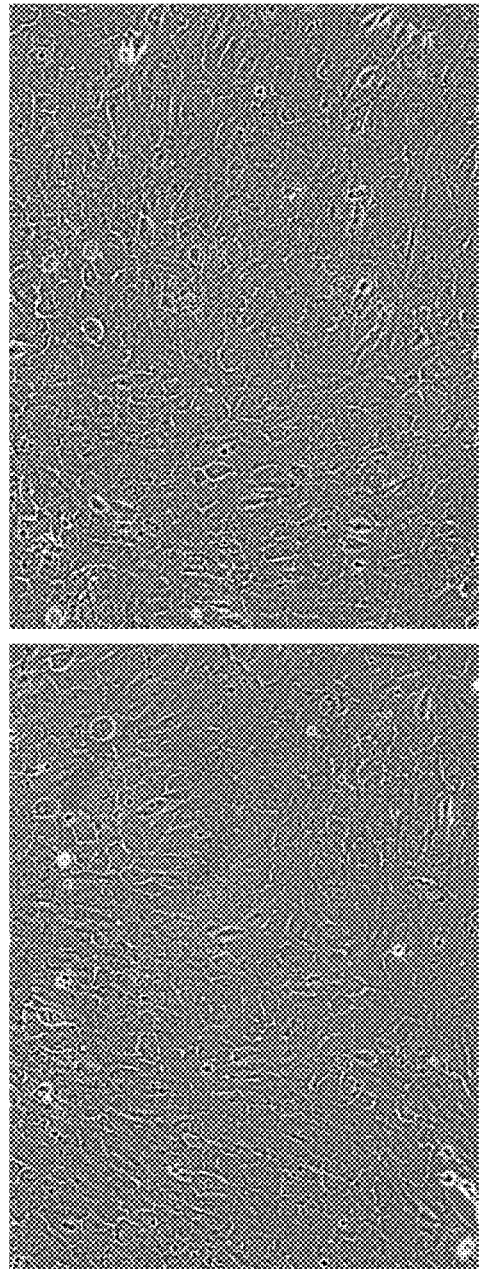
Fig. 1

SEQUENCE LISTING

```
<160> NUMBER OF SEQ ID NOS: 2

<210> SEQ ID NO 1
<211> LENGTH: 21
<212> TYPE: DNA
<213> ORGANISM: artificial sequence
<220> FEATURE:
<223> OTHER INFORMATION: Sense strand of siRNA

<400> SEQUENCE: 1
cauucgcauu caguccauau t                                                 21

<210> SEQ ID NO 2
<211> LENGTH: 21
<212> TYPE: DNA
<213> ORGANISM: artificial sequence
<220> FEATURE:
<223> OTHER INFORMATION: Antisense strand of siRNA

<400> SEQUENCE: 2
uauggacuga augcgaauga t                                                 21
```

MTOR-INHIBITOR-CONTAINING MEDICINE FOR TREATING OR PREVENTING OPHTHALMIC SYMPTOMS, DISORDERS, OR DISEASES, AND APPLICATION THEREOF

TECHNICAL FIELD

The present invention relates to a medicament for treating or preventing eye conditions, disorders, or diseases, comprising an mTOR (also referred to as mechanistic target of rapamycin mammalian target of rapamycin) inhibitor and application thereof.

BACKGROUND ART

Visual information is recognized when light transmitted into the cornea, which is a transparent tissue at the frontmost part of an eye ball, reaches the retina and excites nerve cells of the retina, and a generated electrical signal is transmitted through the optic nerve to the visual cortex of the cerebrum. To attain good vision, it is necessary that the cornea is transparent. The transparency of the cornea is retained by maintaining constant water content with pumping and barrier functions of corneal endothelial cells.

Human corneal endothelial cells are present at a density of about 3000 cells per 1 $mm^2$ at birth. Once damaged, human corneal endothelial cells have a very limited ability to regenerate. Fuchs' endothelial corneal dystrophy is a disease that causes abnormality in endothelial cells inside the cornea and significantly reduces the density of corneal endothelial cells, resulting in edema of the cornea. The cause thereof is unknown. In Fuchs' endothelial corneal dystrophy, extracellular matrix such as collagen or fibronectin is deposited on a part of the back surface of a Descemet's membrane at the back of the cornea, resulting in guttae (Corneal guttae) and hypertrophy of the Descemet's membrane. Guttae (Corneal guttae) and hypertrophy of the Descemet's membrane are the cause of photophobia or blurred vision in Fuchs' endothelial corneal dystrophy patients, which significantly compromises the QOL of the patients. In this manner, extracellular matrix such as fibronectin is associated with conditions that cause reduced visual acuity such as guttata on the corneal endothelial surface or turbid guttae, and can be the main cause of a corneal endothelial disorder associated with opacity of the cornea such as clouding, corneal turbidity or leucoma. It is understood that there is no effective therapeutic method other than corneal transplant for Fuchs' endothelial corneal dystrophy. However, there is a shortage in cornea donation in Japan, where the number of patients waiting for corneal transplant is about 2600, whereas the number of corneal transplants performed in Japan is approximately 1700 annually.

For Fuchs' endothelial corneal dystrophy, culture (Non Patent Literatures 1 and 3) and immortalization (Non Patent Literature 2) of corneal endothelial cells from Fuchs' corneal dystrophy patients have been reported, but cells suitable for screening of a therapeutic drug or progression preventing drug which maintain the features of the disease, such as overproduction of extracellular matrices, have not been reported. Therefore, there is a limit to the development of a therapeutic drug thereof. Currently, there is no therapeutic drug that is used in clinical practice, so that therapy is reliant on corneal transplant.

CITATION LIST

Non Patent Literature

[NPL 1] Zaniolo K, et al. Exp Eye Res.; 94 (1): 22-31. 2012
[NPL 2] Azizi B, et al. Invest Ophthalmol Vis Sci. 2; 52 (13): 9291-9297. 2011
[NPL 3] Kelliher C. et al. Exp Eye Res Vol. 93 (6), 880-888, 2011

SUMMARY OF INVENTION

Solution to Problem

The inventors have discovered that inhibition of an mTOR suppresses cell death (apoptosis) of an eye, especially corneal endothelial cells, and can be applied to the use for treating or preventing ophthalmic diseases such as corneal endothelial disorders (especially corneal endothelial disorders in Fuchs' endothelial corneal dystrophy) due to a transforming growth factor-β (TGF-β). In addition, the inventors have unexpectedly discovered that overexpression of extracellular matrix (ECM) such as fibronectin can be suppressed by inhibiting mTOR. The inventors have thereby discovered that an mTOR inhibitor can be applied to the improvement, therapy, or prevention of corneal endothelial diseases due to overexpression of extracellular matrix (e.g., guttae, hypertrophy of the Descemet's layer, corneal turbidity, leucoma, other conditions of clouding, and the like). Since cell death and extracellular matrix are independent events, it is preferable that both can be suppressed.

The present invention therefore provides, for example, the following items.

(Item 1)
A composition for use in preventing or treating an eye condition, disorder, or disease, comprising an mTOR inhibitor.

(Item 2)
The composition of item 1, wherein the eye condition, disorder, or disease is a corneal endothelial condition, disorder, or disease.

(Item 3)
The composition of item 1 or 2, wherein the eye condition, disorder, or disease is a corneal endothelial condition, disorder, or disease due to a transforming growth factor-β (TGF-β).

(Item 4)
The composition of any one of items 1 to 3, wherein the corneal endothelial condition, disorder, or disease is selected from the group consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

(Item 5)
The composition of any one of items 1 to 4, wherein the corneal endothelial condition, disorder, or disease is due to overexpression of extracellular matrix (ECM).

(Item 6)
The composition of item 5, wherein the corneal endothelial condition, disorder, or disease is selected from the group consisting of Fuchs' endothelial corneal dystrophy, guttae formation, hypertrophy of a Descemet's membrane, hypertrophy of a cornea, turbidity, scar, corneal nebula, corneal macula, corneal leucoma, photophobia, and blurred vision.

(Item 7)

The composition of any one of items 1 to 6, wherein the condition, disorder, or disease comprises Fuchs' endothelial corneal dystrophy.

(Item 8)

The composition of any one of items 1 to 7, wherein the mTOR inhibitor is selected from the group consisting of rapamycin, temsirolimus, everolimus, PI-103, CC-223, INK128, AZD8055, KU 0063794, Voxtalisib, Ridaforolimus, NVP-BEZ235, CZ415, Torkinib, Torin 1, Omipalisib, OSI-027, PF-04691502, Apitolisib, WYE-354, Vistusertib, Torin 2, Tacrolimus, GSK1059615, Gedatolisib, WYE-125132, BGT226, Palomid 529, PP121, WYE-687, CH5132799, WAY-600, ETP-46464, GDC-0349, XL388, Zotarolimus, and Chrysophanic Acid.

(Item 9)

The composition of any one of items 1 to 7, wherein the mTOR inhibitor is an mTOR gene expression suppressing substance.

(Item 10)

The composition of item 9, wherein the mTOR gene expression suppressing substance is siRNA, antisense nucleic acid, or ribozyme against an mTOR gene.

(Item 11)

The composition of item 9 or 10, wherein the mTOR gene expression suppressing substance is siRNA against an mTOR gene, wherein the siRNA comprises a sense strand consisting of a nucleic acid sequence set forth in SEQ ID NO: 1 or the nucleic acid sequence wherein 1 to 3 bases of nucleotides are deleted, substituted, inserted and/or added, and an antisense strand consisting of a nucleic acid sequence set forth in SEQ ID NO: 2 or the nucleic acid sequence wherein 1 to 3 bases of nucleotides are deleted, substituted, inserted and/or added.

(Item 12)

The composition of any one of items 1 to 8, wherein the mTOR inhibitor is selected from the group consisting of rapamycin, temsirolimus, and everolimus.

(Item 13)

The composition of any one of items 1 to 12, wherein the composition is an eye drop.

(Item 14)

The composition of any one of items 1 to 8, wherein the mTOR inhibitor is rapamycin and is present in the composition at at least about 0.1 nM.

(Item 15)

The composition of any one of items 1 to 8, wherein the composition is an eye drop, wherein the mTOR inhibitor is rapamycin and is present in the eye drop at at least about 0.1 mM.

(Item 16)

The composition of any one of items 1 to 8, wherein the mTOR inhibitor is temsirolimus and is present in the composition at at least about 0.01 nM.

(Item 17)

The composition of any one of items 1 to 8, wherein the composition is an eye drop, wherein the mTOR inhibitor is temsirolimus and is present in the eye drop at at least about 0.01 mM.

(Item 18)

The composition of any one of items 1 to 8, wherein the mTOR inhibitor is everolimus and is present in the composition at at least about 0.1 nM.

(Item 19)

The composition of any one of items 1 to 8, wherein the composition is an eye drop, wherein the mTOR inhibitor is everolimus and is present in the eye drop at at least about 0.1 mM.

(Item 1A)

A method for preventing or treating an eye condition, disorder, or disease in a subject, wherein the method comprises administering an effective amount of an mTOR inhibitor to the subject.

(Item 2A)

The method of item 1A, wherein the eye condition, disorder, or disease is a corneal endothelial condition, disorder, or disease.

(Item 3A)

The method of item 1A or 2A, wherein the eye condition, disorder, or disease is a corneal endothelial condition, disorder, or disease due to a transforming growth factor-β (TGF-β).

(Item 4A)

The method of any one of items 1A to 3A, wherein the corneal endothelial condition, disorder, or disease is selected from the group consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

(Item 5A)

The method of any one of items 1A to 4A, wherein the corneal endothelial condition, disorder, or disease is due to overexpression of extracellular matrix (ECM).

(Item 6A)

The method of item 5A, wherein the corneal endothelial condition, disorder, or disease is selected from the group consisting of Fuchs' endothelial corneal dystrophy, guttae formation, hypertrophy of a Descemet's membrane, hypertrophy of a cornea, turbidity, scar, corneal nebula, corneal macula, leucoma, photophobia, and blurred vision.

(Item 7A)

The method of any one of items 1A to 6A, wherein the condition, disorder, or disease comprises Fuchs' endothelial corneal dystrophy.

(Item 8A)

The method of any one of items 1A to 7A, wherein the mTOR inhibitor is selected from the group consisting of rapamycin, temsirolimus, everolimus, PI-103, CC-223, INK128, AZD8055, KU 0063794, Voxtalisib, Ridaforolimus, NVP-BEZ235, CZ415, Torkinib, Torin 1, Omipalisib, OSI-027, PF-04691502, Apitolisib, WYE-354, Vistusertib, Torin 2, Tacrolimus, GSK1059615, Gedatolisib, WYE-125132, BGT226, Palomid 529, PP121, WYE-687, CH5132799, WAY-600, ETP-46464, GDC-0349, XL388, Zotarolimus, and Chrysophanic Acid.

(Item 9A)

The method of any one of items 1A to 7A, wherein the mTOR inhibitor is an mTOR gene expression suppressing substance.

(Item 10A)

The method of item 9A, wherein the mTOR gene expression suppressing substance is siRNA, antisense nucleic acid, or ribozyme against an mTOR gene.

(Item 11A)

The method of item 9A or 10A, wherein the mTOR gene expression suppressing substance is siRNA against an mTOR gene, wherein the siRNA comprises a sense strand consisting of a nucleic acid sequence set forth in SEQ ID NO: 1 or the nucleic acid sequence wherein 1 to 3 bases of nucleotides are deleted, substituted, inserted and/or added, and an antisense strand consisting of a nucleic acid sequence set forth in SEQ ID NO: 2 or a nucleic acid sequence wherein 1 to 3 bases of nucleotides are deleted, substituted, inserted and/or added.
(Item 12A)
The method of any one of items 1A to 8A, wherein the mTOR inhibitor is selected from the group consisting of rapamycin, temsirolimus, and everolimus.
(Item 13A)
The method of any one of items 1A to 12A, wherein the mTOR inhibitor is administered as an eye drop.
(Item 14A)
The method of any one of items 1A to 8A, wherein the mTOR inhibitor is rapamycin and is administered at a concentration of at least about 0.1 nM.
(Item 15A)
The method of any one of items 1A to 8A, wherein the mTOR inhibitor is administered as an eye drop, wherein the mTOR inhibitor is rapamycin and is present in the eye drop at at least about 0.1 mM.
(Item 16A)
The method of any one of items 1A to 8A, wherein the mTOR inhibitor is temsirolimus and is administered at a concentration of at least about 0.01 nM.
(Item 17A)
The method of any one of items 1A to 8A, wherein the mTOR inhibitor is administered as an eye drop, wherein the mTOR inhibitor is temsirolimus and is present in the eye drop at at least about 0.01 mM.
(Item 18A)
The method of any one of items 1A to 8A, wherein the mTOR inhibitor is everolimus and is administered at a concentration of at least about 0.1 nM.
(Item 19A)
The method of any one of items 1A to 8A, wherein the mTOR inhibitor is administered as an eye drop, wherein the mTOR inhibitor is everolimus and is present in the eye drop at at least about 0.1 mM.
(Item 20A)
The method of any one of items 1A to 19A, wherein the mTOR inhibitor is locally administered.
(Item 21A)
The method of any one of items 1A to 20A, wherein the mTOR inhibitor is locally administered to an eye.
(Item 22A)
The method of any one of items 1A to 21A, wherein the mTOR inhibitor is administered so as to contact a cornea.
(Item 1B)
Use of an mTOR inhibitor for manufacturing a medicament for preventing or treating an eye condition, disorder, or disease.
(Item 2B)
The use of item 1B, wherein the eye condition, disorder, or disease is a corneal endothelial condition, disorder, or disease.
(Item 3B)
The use of item 1B or 2B, wherein the eye condition, disorder, or disease is a corneal endothelial condition, disorder, or disease due to a transforming growth factor-β (TGF-β).
(Item 4B)
The use of any one of items 1B to 3B, wherein the corneal endothelial condition, disorder, or disease is selected from the group consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.
(Item 5B)
The use of any one of items 1B to 4B, wherein the corneal endothelial condition, disorder, or disease is due to overexpression of extracellular matrix (ECM).
(Item 6B)
The use of item 5B, wherein the corneal endothelial condition, disorder, or disease is selected from the group consisting of Fuchs' endothelial corneal dystrophy, guttae formation, hypertrophy of a Descemet's membrane, hypertrophy of a cornea, turbidity, scar, corneal nebula, corneal macula, leucoma, photophobia, and blurred vision.
(Item 7B)
The use of any one of items 1B to 6B, wherein the condition, disorder, or disease comprises Fuchs' endothelial corneal dystrophy.
(Item 8B)
The use of any one of items 1B to 7B, wherein the mTOR inhibitor is selected from the group consisting of rapamycin, temsirolimus, everolimus, PI-103, CC-223, INK128, AZD8055, KU 0063794, Voxtalisib, Ridaforolimus, NVP-BEZ235, CZ415, Torkinib, Torin 1, Omipalisib, OSI-027, PF-04691502, Apitolisib, WYE-354, Vistusertib, Torin 2, Tacrolimus, GSK1059615, Gedatolisib, WYE-125132, BGT226, Palomid 529, PP121, WYE-687, CH5132799, WAY-600, ETP-46464, GDC-0349, XL388, Zotarolimus, and Chrysophanic Acid.
(Item 9B)
The use of any one of items 1B to 7B, wherein the mTOR inhibitor is an mTOR gene expression suppressing substance.
(Item 10B)
The use of item 9B, wherein the mTOR gene expression suppressing substance is siRNA, antisense nucleic acid, or ribozyme against an mTOR gene.
(Item 11B)
The use of item 9B or 10B, wherein the mTOR gene expression suppressing substance is siRNA against an mTOR gene, wherein the siRNA comprises a sense strand consisting of a nucleic acid sequence set forth in SEQ ID NO: 1 or the nucleic acid sequence wherein 1 to 3 bases of nucleotides are deleted, substituted, inserted and/or added, and an antisense strand consisting of a nucleic acid sequence set forth in SEQ ID NO: 2 or the nucleic acid sequence wherein to 3 bases of nucleotides are deleted, substituted, inserted and/or added.
(Item 12B)
The use of any one of items 1B to 8B, wherein the mTOR inhibitor is selected from the group consisting of rapamycin, temsirolimus, and everolimus.
(Item 13B)
The use of any one of items 1B to 12B, wherein the medicament is an eye drop.
(Item 14B)
The use of any one of items 1 to 8, wherein the mTOR inhibitor is rapamycin and is present in the medicament at at least about 0.1 nM.
(Item 15B)
The use of any one of items 1B to 8B, wherein the medicament is an eye drop, wherein the mTOR inhibitor is rapamycin and is present in the eye drop at at least about 0.1 mM.

(Item 16B)

The use of any one of items 1B to 8B, wherein the mTOR inhibitor is temsirolimus and is present in the medicament at at least about 0.01 nM.

(Item 17B)

The use of any one of items 1B to 8B, wherein the medicament is an eye drop, wherein the mTOR inhibitor is temsirolimus and is present in the eye drop at at least about 0.01 mM.

(Item 18B)

The use of any one of items 1B to 8B, wherein the mTOR inhibitor is everolimus and is present in the medicament at at least about 0.1 nM.

(Item 19B)

The use of any one of items 1B to 8B, wherein the medicament is an eye drop, wherein the mTOR inhibitor is everolimus and is present in the eye drop at at least about 0.1 mM.

(Item 1C)

An mTOR inhibitor for use in preventing or treating an eye condition, disorder, or disease.

(Item 2C)

The mTOR inhibitor of item 1C, comprising one or more features of the items above.

(Item 1D)

A composition for preserving corneal endothelial cells, comprising an mTOR inhibitor.

(Item 2D)

The composition of item 1D, comprising one or more features of the items above.

(Item 1E)

A method for preserving corneal endothelial cells, comprising contacting an effective amount of an mTOR inhibitor with corneal endothelial cells.

(Item 2E)

The method of item 1E, comprising one or more features of the items above.

(Item 1F)

A method for growing corneal endothelial cells or promoting growth of corneal endothelial cells, encompassing contacting an effective amount of an mTOR inhibitor with corneal endothelial cells.

(Item 2F)

The method of item 1E, comprising one or more features of the items above.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

The present invention unexpectedly discovered that an mTOR inhibitor may treat or prevent a disease due to a disorder or a disease due to transforming growth factor-β (TGF-β) in Fuchs' endothelial corneal dystrophy or the like and can provide a medicament that may treat or prevent an eye condition, disorder, or disease including such a disease. The present invention also provides a medicament that can treat or prevent a disease, due to a corneal endothelial disorder due to overproduction of extracellular matrix (e.g., fibronectin), such as guttae, hypertrophy of the Descemet's membrane, corneal turbidity, leucoma or other conditions of clouding. The present invention further provides a composition for preserving corneal endothelial cells or a composition for promoting the growth of corneal endothelial cells, comprising an mTOR inhibitor, as well as a method for preserving and/or growing or promoting the growth of corneal endothelial cells.

BRIEF DESCRIPTION OF DRAWINGS

FIG. 1 shows microscopic images of iFECDs. The top left image shows a control group wherein TGF-β2 is not supplemented, the top right image shows a group wherein TGF-β2 is supplemented, the bottom left image shows a group wherein TGF-β2 and rapamycin are supplemented, and the bottom right image shows a group wherein TGF-β2 and Z-VD-FMK, which is a caspase inhibitor, are supplemented.

DESCRIPTION OF EMBODIMENTS

Figure 2:
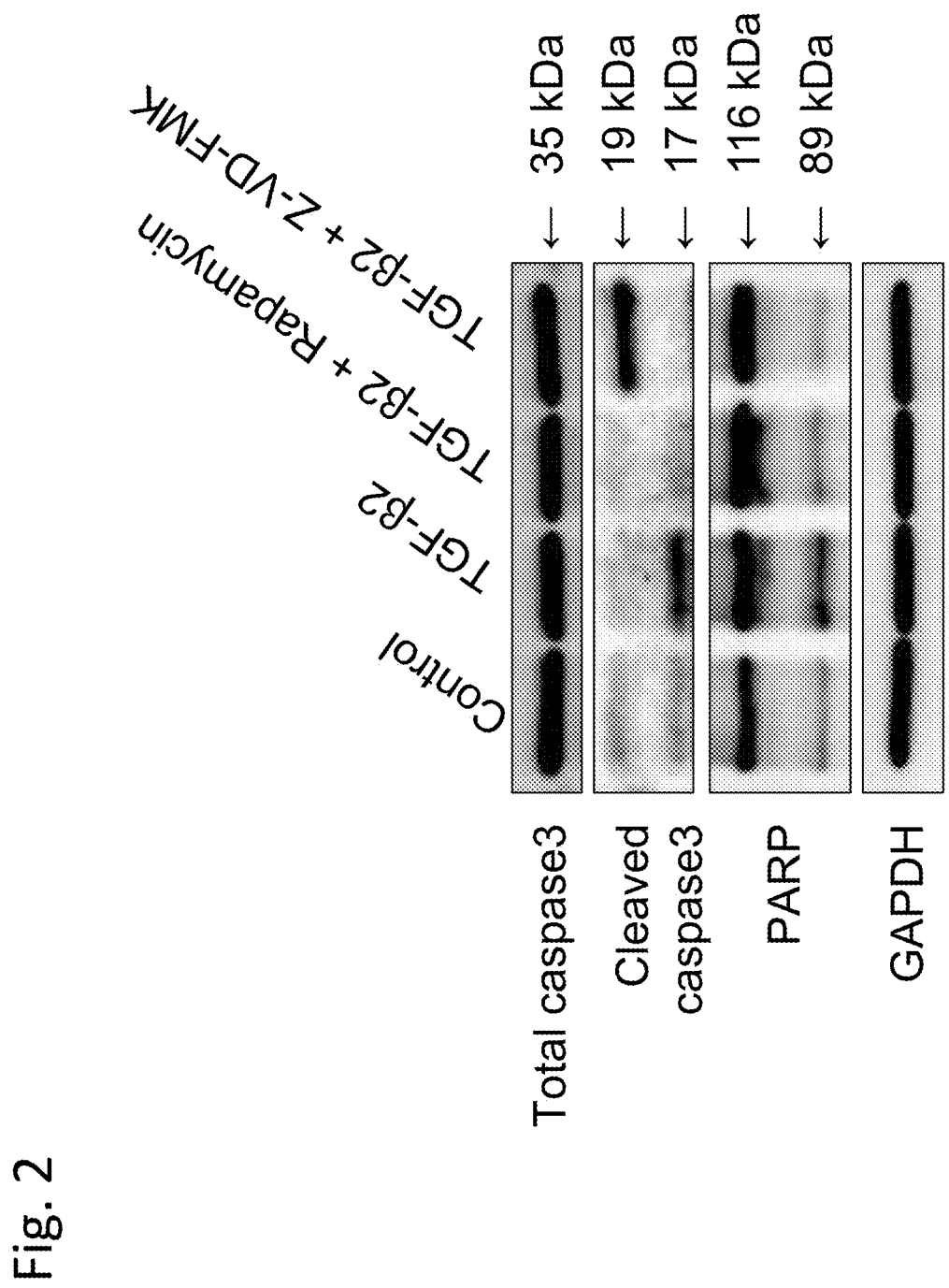
FIG. 2 shows the results of western blot on total caspase 3, cleaved caspase 3, PARP and GAPDH. The figure shows, from the left, a control group wherein TGF-β2 is not supplemented, a group wherein TGF-β2 is supplemented, a group wherein TGF-β2 and rapamycin are supplemented, and a group wherein TGF-β2 and Z-VD-FMK, which is a caspase inhibitor, are supplemented.

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definition

As used herein, "about" before a numerical value means±10% of the numerical value that follows.

As used herein, "mTOR inhibitor" refers to any agent that inhibits signaling of mTOR. An mTOR inhibitor is preferably water-soluble. This is because, unless an mTOR inhibitor is water-soluble, it may be necessary to use a solvent that is not highly biocompatible. Water-solubility can be classified based on the definition of solubility in the pharmacopoeia. In other words, the amount of solvent required to dissolve 1 g or 1 mL of solute is defined as extremely readily dissolvable: less than 1 mL; readily dissolvable: 1 mL or greater and less than 10 mL; somewhat readily dissolvable: 10 mL or greater and less than 30 mL; somewhat difficult to dissolve: 30 mL or greater and less than 100 mL; difficult to dissolve: 100 mL or greater and less than 1000 mL; very difficult to dissolve: 1000 mL or greater and less than 10000 mL; and hardly dissolvable: 10000 mL or greater. Solubility is similarly assessed herein. Water solubility is understood to mean that a substance with any solubility can be used, as long as an effective amount thereof can be dissolved when water is used as a solvent. Such a water-soluble component is advantageously used as an eye drop.

An mTOR (mammalian target of rapamycin) is a serine/threonine kinase identified as a target molecule of rapamycin and is considered to play a central role in the adjustment of cell division, survival and the like. An mTOR is also known as SKS; FRAP; FRAP1; FRAP2; RAFT1; RAPT1, and 2475 is given as a Gene ID of NCBI. Based on such information, those skilled in the art can design and manufacture various mTOR inhibitors.

The mTOR inhibitors that can be used in the present invention are not particularly limited, as long as they are compounds having mTOR inhibiting activity. Examples thereof include, rapamycin, temsirolimus, everolimus, PI-103, CC-223, INK128, AZD8055, KU 0063794, Voxtalisib (XL765, SAR245409), Ridaforolimus (Deforolimus, MK-8669), NVP-BEZ235, CZ415, Torkinib (PP242), Torin 1, Omipalisib (GSK2126458, GSK458), OSI-027, PF-04691502, Apitolisib (GDC-0980, RG7422), WYE-354, Vistusertib (AZD2014), Torin 2, Tacrolimus (FK506), GSK1059615, Gedatolisib (PF-05212384, PKI-587), WYE-125132 (WYE-132), BGT226 (NVP-BGT226), Palomid 529 (P529), PP121, WYE-687, CH5132799, WAY-600, ETP-46464, GDC-0349, XL388, Zotarolimus (ABT-578), and Chrysophanic Acid.

Preferred mTOR inhibitors include, but are not limited to, rapamycin, temsirolimus and everolimus. Although not wishing to be bound by any theory, this is because these pharmaceutical products are approved by FDA, PMDA, and the like and problems in the aspects of safety and toxicity are minimized. An ever more preferable mTOR inhibitor is rapamycin. Another preferable mTOR inhibitor is temsirolimus. Another preferable mTOR inhibitor is, but is not limited to, everolimus.

Other examples of mTOR inhibitors that can be used in the present invention include neutralizing antibodies against mTORs, compounds inhibiting the activity of mTORs, compounds inhibiting the transcription of a gene encoding an mTOR (e.g., antisense nucleic acids, siRNAs, ribozymes), peptides, compounds with a plant component, a component of traditional medicament such as Kampo medicine, or other components, and the like.

Antisense nucleic acids used in the present invention may inhibit the expression and/or function of a gene (nucleic acids) encoding a member of a signaling pathway of an mTOR or the like by any of the above-described action. As one embodiment, designing an antisense sequence complementary to an untranslated region near the 5' end of mRNA of a gene encoding the aforementioned mTOR is considered effective for inhibiting translation of a gene. Further, a sequence that is complementary to an untranslated region of 3' or a coding region can also be used. In this manner, antisense nucleic acids utilized in the present invention include not only a translation region of a gene encoding the aforementioned mTOR or the like, but also nucleic acids comprising an antisense sequence of a sequence of an untranslated region. An antisense nucleic acid to be used is linked to the downstream of a suitable promoter, and preferably a sequence comprising a transcription termination signal is linked to the 3' side. A nucleic acid prepared in this manner can be transformed into a desired animal (cell) by using a known method. A sequence of an antisense nucleic acid is preferably a sequence that is complementary to a gene encoding an mTOR of the animal (cell) to be transformed or a portion thereof. However, such a sequence does not need to be fully complementary, as long as gene expression can be effectively suppressed. A transcribed RNA preferably has complementarity that is 90% or greater, and most preferably 95% or greater, with respect to a transcript of a target gene. In order to effectively inhibit the expression of a target gene using an antisense nucleic acid, it is preferable that the length of the antisense nucleic acid is at least 12 bases and less than 25 bases. However, the antisense nucleic acid of the present invention is not necessarily limited to this length. For example, the length may be 11 bases or less, 100 bases or more, or 500 bases or more. An antisense nucleic acid may be composed of only DNA, but may comprise a nucleic acid other than DNAs, such as a locked nucleic acid (LNA). As one embodiment, an antisense nucleic acid used in the present invention may be an LNA containing antisense nucleic acid comprising LNA at the 5' end or LNA at the 3' end. In an embodiment using an antisense nucleic acid in the present invention, the antisense sequence can be designed based on a nucleic acid sequence of an mTOR by using the method described in, for example, Hirashima and Inoue, Shin-seikagaku Jikkenn Kouza 2 [*New Biochemical Experiment Course* 2] Kakusan IV Idenshi no Fukusei to Hatsugen [*Duplication and Expression of Gene of Nucleic Acid IV*], Ed. by the Japanese Biochemical Society, Tokyo Kagaku Dojin, 1993, 319-347.

Expression of mTOR can also be inhibited by utilizing a ribozyme or DNA encoding a ribozyme. A ribozyme refers to an RNA molecule having catalytic activity. While there are ribozymes with various activities, a study focusing on especially ribozymes as an enzyme for cleaving an RNA made it possible to design a ribozyme that site-specifically cleaves an RNA. There are ribozymes with a size of 400 nucleotides or more as in group I intron ribozymes and M1 RNA contained in RNase P, but there are also those with an active domain of about 40 nucleotides called hammerhead or hair-pin ribozymes (Makoto Koizumi and Eiko Otsuka, Protein, Nucleic Acid and Enzyme, 1990, 35, 2191).

For example, a self-cleaving domain of a hammerhead ribozyme cleaves the 3' side of C15 of a sequence called G13U14C15. Base pair formation of U14 and A9 is considered important for the activity thereof. It is also demonstrated that cleavage can also be made at A15 or U15 instead of C15 (Koizumi, M. et al., FEBS Lett, 1988, 228, 228.) Restriction enzyme-like RNA-cleaving ribozymes that recognize the sequence UC, UU, or UA in the target RNAs can be created by designing their substrate-binding sites to be complementary to an RNA sequence near the target site (Koizumi, M. et al., FEBS Lett, 1988, 239, 285., Makoto Koizumi and Eiko Otsuka, Protein, Nucleic Acid and Enzyme, 1990, 35, 2191., Koizumi, M. et al., Nucl. Acids Res., 1989, 17, 7059.)

Hairpin ribozymes are also useful for the objective of the present invention. Such a ribozyme is found, for example, in the minus strand of a tobacco ringspot virus satellite RNA (Buzayan, J M., Nature, 1986, 323, 349). It is demonstrated that target specific RNA-cleaving ribozymes can also be created from hairpin ribozymes (Kikuchi, Y. & Sasaki, N., Nucl. Acids Res, 1991, 19, 6751., Yo Kikuchi, Kagaku to Seibutsu [*Chemistry and Biology*], 1992, 30, 112). In this manner, expression of a gene encoding an mTOR or the like can be inhibited by specifically cleaving a transcript of the gene by using a ribozyme.

Expression of an endogenous gene of an mTOR can also be suppressed by RNA interference (hereinafter, abbreviated as "RNAi") using a double-stranded RNA having a sequence that is identical or similar to a target gene sequence. RNAi is a methodology that is currently drawing attention, which can suppress the expression of a gene having a sequence that is homologous to a double-stranded RNA (dsRNA) when the dsRNA is incorporated directly into a cell. In mammalian cells, short stranded dsRNA (siRNA) can be used to induce RNAi. RNAi has many advantages over knockout mice, such as a stable effect, facilitated experiment, and low cost. SiRNA is discussed in detail in other parts of the specification.

As used herein "siRNA" is an RNA molecule having a double-stranded RNA portion consisting of 15 to 40 bases, where siRNA has a function of cleaving mRNA of a target gene with a sequence complementary to an antisense strand of the siRNA to suppress the expression of the target gene. Specifically, the siRNA in the present invention is an RNA comprising a double-stranded RNA portion consisting of a sense RNA strand consisting of a sequence homologous to consecutive RNA sequences in mRNA of mTOR and an antisense RNA strand consisting of a sequence complementary to the sense RNA sequence. Design and manufacture of such siRNA and mutant siRNA discussed below are within the technical competence of those skilled in the art. Any consecutive RNA regions of mRNA which is a transcript of a sequence of mTOR can be appropriately selected to make double-stranded RNA corresponding to this region, which is within the ordinary procedure performed by those skilled in the art. Further, those skilled in the art can appropriately select an siRNA sequence having a stronger RNAi effect from mRNA sequences, which are transcripts of the sequence, by a known method. Further, if one of the strands is revealed, those skilled in the art can readily find the base sequence of the other stand (complementary strand). SiRNA can be appropriately made by using a commercially available nucleic acid synthesizer. A common synthesis service can also be utilized for desired RNA synthesis.

In terms of bases, the length of a double-stranded RNA portion is 15 to 40 bases, preferably 15 to 30 bases, more preferably 15 to 25 bases, still more preferably 18 to 23 bases, and most preferably 19 to 21 bases. It is understood that the upper limits and the lower limits thereof are not limited to such specific limits, and may be of any combination of the mentioned limits. The end structure of a sense strand or antisense strand of siRNA is not particularly limited, and can be appropriately selected in accordance with the objective. For example, such an end structure may have a blunt end or a sticky end (overhang). A type where the 3' end protrudes out is preferred. SiRNA having an overhang consisting of several bases, preferably 1 to 3 bases, and more preferably 2 bases at the 3' end of a sense RNA strand and antisense RNA strand is preferable for having a large effect of suppressing expression of a target gene in many cases. The type of bases of an overhang is not particularly limited, which may be either a base constituting an RNA or a base constituting a DNA. An example of a preferred overhang sequence includes dTdT at the 3' end (2 bp of deoxy T) and the like. Examples of preferable siRNA include, but are not limited to, all siRNAs with dTdT (2 bp of deoxy T) at the 3' end of the sense or antisense strands of the siRNA.

Furthermore, it is also possible to use siRNA in which one to several nucleotides are deleted, substituted, inserted and/or added at one or both of the sense strand and antisense strand of the siRNA described above. One to several bases as used herein is not particularly limited, but preferably refers to 1 to 4 bases, more preferably 1 to bases, and most preferably 1 to 2 bases. Specific examples of such mutations include, but are not limited to, mutations resulting in 0 to 3 bases at the 3'-overhang portion, mutations that change the base sequence of the 3'-overhang portion to another base sequence, mutations in which the lengths of the above-described sense RNA strand and antisense RNA strand are different by 1 to 3 bases due to insertion, addition or deletion of bases, mutations substituting a base in the sense strand and/or the antisense with another base, and the like. However, it is necessary that the sense strand and the antisense strand can hybridize in such mutant siRNAs, and these mutant siRNAs have the ability to suppress gene expression that is equivalent to that of siRNAs without any mutations.

SiRNA may also be a molecule with a structure in which one end is closed, such as siRNA with a hairpin structure (Short Hairpin RNA; shRNA). A shRNA is an RNA comprising a sense strand RNA with a specific sequence of a target gene, an antisense strand RNA consisting of a sequence complementary to the sense strand sequence, and a linker sequence for connecting the two strands, wherein the sense strand portion hybridizes with the antisense strand portion to form a double-stranded RNA portion.

It is desirable for siRNA to not exhibit the so-called off-target effect in clinical use. An off-target effect refers to an action for suppressing the expression of another gene, besides the target gene, which is partially homologous to the siRNA used. In order to avoid an off-target effect, it is possible to confirm that a candidate siRNA does not have cross reactivity by using a DNA microarray or the like in advance. Further, it is possible to avoid an off-target effect by confirming whether there is a gene comprising a moiety that is highly homologous to a sequence of a candidate siRNA, other than a target gene, using a known database provided by the NCBI (National Center for Biotechnology Information) or the like.

In order to make the siRNA according to the present invention, a known method, such as a method using chemical synthesis or a method using a gene recombination technique, can be appropriately used. With a method using synthesis, a double-stranded RNA can be synthesized based on sequence information by using a common method. With a method using a gene recombination technique, a siRNA can be made by constructing an expression vector encoding a sense strand sequence or an antisense strand sequence and introducing the vector into a host cell, and then obtaining each of sense strand RNA and antisense strand RNA produced by transcription. It is also possible to make a desired double-stranded RNA by expressing an shRNA forming a hairpin structure, comprising a sense strand of a specific sequence of a target gene, an antisense strand consisting of a sequence complementary to the sense strand sequence, and a linker sequence for linking the two strands.

For a siRNA, all or part of the nucleic acid constituting the siRNA may be a natural or a modified nucleic acid, as long as such a nucleic acid has activity to suppress the expression of a target gene.

The siRNA according to the present invention does not necessarily have to be a pair of double-stranded RNAs to a target sequence. It may be a mixture of a plurality of pairs (the "plurality" is not particularly limited, but preferably refers to a small number of about 2 to 5) of double-stranded RNAs to a region comprising a target sequence. In this regard, those skilled in the art can appropriately make an siRNA as a nucleic acid mixture corresponding to a target sequence by using a commercially available nucleic acid synthesizer and a DICER enzyme. A common synthesis service can also be utilized for desired RNA synthesis. It should be noted that the siRNA according to the present invention encompasses the so-called "cocktail siRNA". For the siRNA according to the present invention, not all the nucleotides have to be a ribonucleotide (RNA). In other words, in the present invention, one or plurality of ribonucleotides constituting an siRNA may be a corresponding deoxyribonucleotide. This term "corresponding" refers to having the same base type (adenine, guanine, cytosine, thymine (uracil)) but a different sugar moiety structure. For example, a deoxyribonucleotide corresponding to a ribonucleotide having adenine refers to a deoxyribonucleotide having adenine.

Furthermore, a DNA (vector) which can express the above-described RNA according to the present invention is also encompassed as a preferred embodiment of a nucleic acid which can suppress the expression of an mTOR or the like. For example, the DNA (vector) which can express the above-described double-stranded RNA according to the present invention is a DNA having a structure in which a DNA encoding one of the strands of the double-stranded RNA and a DNA encoding the other strand of the double-stranded RNA are linked to a promoter so that each of the DNAs can be expressed. The above-described DNA according to the present invention can be appropriately made by those skilled in the art by using a common genetic engineering technique. More specifically, the expression vector according to the present invention can be made by appropriately inserting a DNA encoding the RNA of interest into various known expression vectors.

In the present invention, a modified nucleic acid may be used as a nucleic acid for suppressing the expression of a target gene. A modified nucleic acid refers to a nucleic acid, which has a modification at a nucleoside (base moiety, sugar moiety) and/or an inter-nucleoside binding site and has a structure that is different from that of a naturally occurring nucleic acid. Examples of "modified nucleoside" constituting a modified nucleic acid include: abasic nucleosides; arabinonucleoside, 2'-deoxyuridine, α-deoxyribonucleoside, β-L-deoxyribonucleoside, and other sugar modification bearing nucleosides; peptide nucleic acids (PNA), phosphate group-binding peptide nucleic acids (PHONA), locked nucleic acids (LNA), morpholino nucleic acids and the like. The above sugar modification bearing nucleosides include 2'-O-methylribose, 2'-deoxy-2'-fluororibose, 3'-O-methylribose and other substituted pentose; 1',2'-deoxyribose; arabinose; substituted arabinose sugar; and nucleoside having a sugar modification of alpha-anomer and hexose. These nucleosides may be a modified base in which the base moiety is modified. Examples of such modified bases include pyrimidine such as 5-hydroxycytosine, 5-fluorouracil, and 4-thiouracil; purine such as 6-methyladenine and 6-thioguanosine; other heterocyclic bases and the like.

Examples of a "modified inter-nucleoside bond" which constitutes a modified nucleic acid include alkyl linker, glyceryl linker, amino linker, poly(ethylene glycol) bond, inter-methyl phosphonate nucleoside bond; and bonds between non-natural nucleosides such as methylphosphonothioate, phosphotriester, phosphothiotriester, phosphorothioate, phosphorodithioate, triester prodrug, sulfone, sulfonamide, sulfamate, formacetal, N-methylhydroxylamine, carbonate, carbamate, morpholino, boranophosphonate, and phosphoramidate.

The nucleic acid sequence comprised in the double-stranded siRNA according to the present invention includes siRNAs for an mTOR, other mTOR signaling members and the like.

It is also possible to introduce the nucleic acid or agent according to the present invention into a phospholipid endoplasmic reticulum such as a liposome and administer the endoplasmic reticulum. An endoplasmic reticulum in which an siRNA or shRNA is retained can be introduced into a predetermined cell using lipofection. The resulting cell is then systemically administered, such as intravenously, intra-arterially or the like. It can also be locally administered to a required site in an eye or the like. While an siRNA exhibits a very good specific, post-transcription suppressing effect in vitro, the siRNA is quickly degraded in vivo due to nuclease activity in the serum so that the duration thereof is limited. Therefore, there has been a need for the development of a better and more effective delivery system. As an example, Ochiya, T et al., Nature Med., 5: 707-710, 1999, Curr. Gene Ther., 1: 31-52, 2001 reports that a biocompatible material atelocollagen, when mixed with a nucleic acid to form a complex, is a carrier which has an action of protecting a nucleic acid from a degrading enzyme in a living organism and is extremely suitable as a carrier for an siRNA. While such a form can be used, the method for introducing a nucleic acid, therapeutic or prophylactic drug according to the present invention is not limited thereto. In this manner, due to the fast degradation by the action of a nuclease in the serum in a living organism, it becomes possible to achieve continuation of an effect for an extended period of time. For example, Takeshita F. PNAS, (2003) 102 (34) 12177-82, Minakuchi Y Nucleic Acids Research (2004) 32 (13) e109 report that atelocollagen derived from bovine skin forms a complex with a nucleic acid, which has action of protecting a nucleic acid from a degrading enzyme in a living organism and is extremely suitable as a carrier for an siRNA. Such a technique can be used.

As used herein, "iFECD" (immortalized Fuchs' endothelial corneal dystrophy) is an abbreviation for immortalized Fuchs' endothelial corneal dystrophy cells. A manufacturing method of iFECD is described in, for example, WO 2015/015655.

As used herein, "HCEC" (human corneal endothelial cells) is an abbreviation for human corneal endothelial cells. In addition, "iHCEC" is an abbreviation for immortalized human corneal endothelial cells.

As used herein, "programmed cell death" refers to a phenomenon of cells spontaneously dying at a determined time or environment as if the death is pre-programmed. Programmed cell death is used in the meaning that includes, for example, "apoptosis".

As used herein, "transforming growth factor-β (also denoted with the abbreviation TGF-β)" is used in the same meaning as those used in the art. It is a homodimer multi-functional cytokine with a molecular weight of 25 kD exhibiting a variety of biological activity, such as being responsible for pathogenesis of various sclerotic diseases, rheumatoid arthritis, and proliferative vitreoretinopathy, being deeply involved in hair loss, suppressing the functioning of immunocompetent cells while suppressing over-production of protease to prevent degradation of pulmonary tissue resulting in pulmonary emphysema, and suppressing cancer cell growth. "TGF-β signal" refers to a signal mediated by TGF-β, which is elicited by TGF-β. Examples of TGF-β signals include signals mediated by TGF-β2 in addition to signals mediated by TGF-β1, TGF-β3 or the like. In humans, TGF-β has three isoforms, TGF-β1 to β3, which have homology of about 70% and similar action. TGF-β is produced as an inactive latent form with a molecular weight of about 300 kD which is unable to bind to a receptor. The action thereof is exerted by being activated on a target cell surface or the surroundings thereof to become an active form that can bind to a receptor.

Although not wishing to be bound by any theory, the action of TGF-β in a target cell is understood to be transmitted by a phosphorylation pathway of a series of proteins responsible for transmitting information called Smad. First, when activated TGF-β binds to a TGF-β type II receptor on a target cell surface, a receptor complex consisting of two molecules of type II receptors and two molecules of TGF-β type I receptors is formed, and the type II receptors phosphorylate the type I receptors. It is understood that when the phosphorylated type I receptors phosphorylate Smad2 or Smad3, the phosphorylated Smad2 or Smad3 forms a complex with Smad4, where the complex migrates to a nucleus and binds to a target sequence called CAGA box that is present in a target gene promotor region to induce transcription and expression of a target gene with a coactivator.

A transforming growth factor-β (TGF-β) signaling pathway can modulate many cellular activities, such as cell growth and differentiation, growth arrest, programmed cell death, and epithelial mesenchymal transition (EMT), by modulating the target gene. Members of the TGF-β family including TGF-β itself (e.g., TGF-β1, TGF-β2, and TGF-β3), activin, and bone morphogenetic proteins (BMP) are potent modulators of cell growth, differentiation, migration, programmed cell death, and the like.

TGF-β is a protein of about 24 Kd produced by many cells including B lymphocytes, T lymphocytes, and activated macrophages and by many other cell types. Effects of TGF-β on the immune system include IL-2 receptor induction, inhibition of IL-1 induced thymocyte growth, and blocking of IFN-γ induced macrophage activation. TGF-β is considered to be involved in various pathological conditions (Border et al. (1992) J. Clin. Invest. 90:1) and is thoroughly proven to function as either a tumor suppressing substance or a tumor promotor.

Signaling of TGF-β is mediated by two serine/threonine kinase cell surface receptors TGF-βRII and ALK5. TGF-β signaling is initiated by ligand induced receptor dimerization enabling TGF-βRII to phosphorylate an ALK5 receptor. The phosphorylation activates ALK5 kinase activity, and the activated ALK5 then phosphorylates a downstream effector Smad protein (vertebrate homologue of MAD or "Mothers against DPP (decapentaplegic)" protein), Smad2 or Smad3. A p-Smad2/3 complex with Smad4 enters a nucleus and activates transcription of a target gene.

Smad3 is a member of the R-Smad (receptor-activated Smad) subgroup of Smad and a direct mediator of transcription activation by a TGF-β receptor. A TGF-β stimulation results in phosphorylation and activation of Smad2 and Smad3, which form a complex with Smad4 ("common Smad" or "co-Smad" in vertebrates). This accumulates with the nucleus and modulates transcription of a target gene. R-Smad is localized in a cytoplasm and forms a complex with co-Smad through ligand induced phosphorylation by a TGF-β receptor, migrates to the nucleus, where it modulates gene expression associated with a cooperative transcription factor and chromatin. Smad6 and Smad7 are inhibitory Smad ("I-Smad"), i.e., they are transcriptionally induced by TGF-β and function as a TGF-β signaling inhibitor (Feng et al. (2005) Annu. Rev. Cell. Dev. Biol. 21: 659). Smad6/7 obstruct receptor-mediated activation of R-Smad to exert an inhibitory effect thereof; and they are associated with a type I receptor, which competitively obstructs mobilization and phosphorylation of R-Smad. Smad6 and Smad7 are known to replenish E3 ubiquitin ligase, which induces ubiquitination and degradation of Smad6/7 interacting proteins.

TGF-β signaling pathways also have other pathways using transmission by BMP-7 or the like, which go through ALK-1/2/3/6 to express a function via Smad1/5/8. For TGF-β signaling pathways, see J. Massagu'e, Annu. Rev. Biochem. 1998. 67: 753-91; Vilar J M G, Jansen R, Sander C (2006) PLoS Comput Biol 2(1): e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152: 159-166 and the like.

As used herein, "eye condition, disorder, or disease" refers to any condition, disorder, or disease in an eye. An eye condition, disorder, or disease is a condition, disorder, or disease in, for example, the retina, vitreous humor, lens, cornea, sclera, or different portion of the eye. The mTOR inhibitor in the present invention may be especially effective against corneal endothelial condition, disorder, or disease.

As used herein, "corneal endothelial condition, disorder, or disease due to transforming growth factor-β (TGF-β)" refers to any corneal endothelial condition, disorder, or disease induced by TGF-β in corneal endothelial cells. In the present invention, exposure of corneal endothelial cells such as model cells of Fuchs' endothelial corneal dystrophy (e.g., iFECD) to TGF-β2 surprisingly resulted in various disorders (e.g., programmed cell death). This is a phenomenon that had not been well understood conventionally. The inventors, after further analysis of the corneal endothelial condition, disorder, or disease due to a TGF-β signal, unexpectedly discovered that this disorder can be suppressed with an mTOR inhibitor. A corneal endothelial condition, disorder, or disease due to a TGF-β signal is associated with a different signaling pathway of mTOR. Examples of corneal endothelial conditions, disorders, or diseases due to a TGF-β signal include, but are not limited to, Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, cytomegalovirus corneal endotheliitis and the like in which TGF-β expression is observed. Since the disorder discovered in the present invention or a disorder associated therewith is considered expressed or raised especially in corneal endothelial cells or corneal endothelial tissue with higher than normal TGF-β2 expression, any corneal endothelial condition, disorder, or disease in which such corneal endothelial cells or corneal endothelial tissue are observed are especially intended as the target of the present invention.

As used herein, "overexpression of extracellular matrix in corneal endothelial cells" refers to expression of extracellular matrix at an abnormal level compared to extracellular matrix expression levels in normal corneal endothelial cells. "Expression of extracellular matrix at an abnormal level" refers to production of extracellular matrix proteins such as fibronectin at an amount greater than the amount produced in extracellular matrix in a normal form. The production status includes no stimulation, as well as increased amount of expression due to a response to transforming growth factor (TGF) β as needed. For example, this can be about 1.1 fold or greater, about 1.2 fold or greater, about 1.3 fold or greater, about 1.4 fold or greater, about 1.5 fold or greater, about 1.6 fold or greater, about 1.7 fold or greater, about 1.8 fold or greater, about 1.9 fold or greater, or about 2.0 fold or greater with respect to the amount of extracellular matrix under normal circumstances for human corneal endothelial cells. The difference relative to normal is preferably, but not necessarily, statistically significant. It is sufficient that the difference is a medically significant difference.

As used herein, "corneal endothelial disorder due to overexpression of extracellular matrix (ECM)" or a "condition" thereof is mainly a disorder associated with hypertrophy, deposition, clouding due to extracellular matrix or the like, or a condition thereof, which results in guttata on the corneal endothelium surface, hypertrophy of the Descemet's membrane such as turbid guttae of the Descemet's membrane, or the like, and is associated with a condition that causes reduced vision. In corneal endothelial disorders such as Fuchs' corneal dystrophy, overproduction of extracellular matrix worsens the vision or visual sense even without a reduction in cell count, unlike exacerbation in a condition due to death (especially apoptosis) of corneal endothelial cells. Thus, even if cell death can be suppressed, this needs to be addressed. "Corneal endothelial disorder due to overproduction of extracellular matrix (ECM)" and "condition" thereof include, but are not limited to, turbidity, scar, corneal nebula, corneal macula, corneal leucoma, and the like.

In a preferred embodiment, the conditions, disorders, or diseases targeted by the present invention are disorders related to Fuchs' endothelial corneal dystrophy. It is demonstrated that TGF-β induction in corneal endothelial cells is involved in Fuchs' endothelial corneal dystrophy. It is also demonstrated that TGF-β induction may be involved in cell loss in FECDs. Therefore, inhibition of a TGF-β signaling pathway is naturally expected to be an effective therapy for FECDs. However, the inventors unexpectedly found that an mTOR inhibitor can suppress a disorder due to a TGF-β signal.

Since the medicament of the present invention can treat cell damage or the like that is induced by TGF-β2, which can be one of the major causes of abnormalities or disorders in Fuchs' endothelial corneal dystrophy, the medicament is understood to be useful in treating or preventing Fuchs' endothelial corneal dystrophy. In particular, the present invention was able to suppress cell damage or programmed cell death induced by TGF-β2 in a Fuchs' endothelial corneal dystrophy model in the Examples, so that the present invention can be considered usable in therapy for patients with a severe TGF-β2 associated disease in a Fuchs' endothelial corneal dystrophy model. The medicament of the present invention can also, unexpectedly, suppress overexpression of extracellular matrix (ECM), so that the medicament can treat or prevent a disorder or the like in corneal endothelia such as ECM deposition in the Descemet's membrane. Therefore, the present invention can treat or prevent damage to corneal endothelial cells in Fuchs' endothelial corneal dystrophy, decreased corneal endothelial density, guttae formation, hypertrophy of the Descemet's membrane, hypertrophy of a cornea, corneal epithelial disorder, turbidity, scar, turbidity in corneal stroma, photophobia, blurred vision, visual impairment, ophthalmalgia, epiphora, hyperemia, pain, bullous keratopathy, eye discomfort, diminished contrast, halo, glare, edema of the corneal stroma, and the like.

(General Techniques)

Molecular biological methodology, biochemical methodology, microbiological methodology used herein are well known and conventionally used in the art, which are described for example in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [Experimental Medicine, Supplemental Volume], Idenshi Donyu & Hatsugen Kaiseki Jikken Ho [Experimental Methods for Transgenesis & Expression Analysis], Yodosha, 1997, or the like. The reports by Nancy Joyce et al {Joyce, 2004 #161} and {Joyce, 2003 #7} are well known for corneal endothelial cells. However, as discussed above, long-term culture or subculture results in fibroblast-like transformation, and research for an effective culturing method are currently ongoing. Relevant portions thereof (which may be the entire document) are incorporated herein by reference.

DESCRIPTION OF PREFERRED EMBODIMENTS

The preferred embodiments of the present invention are described hereinafter. It is understood that the embodiments are exemplification of the present invention, so that the scope of the present invention is not limited to such preferred embodiments. It should be understood that those skilled in the art can refer to the following preferred embodiments to readily make modifications or changes within the scope of the present invention. Any of these embodiments of the present invention can be appropriately combined by those skilled in the art.

<Medicament>

In one aspect, the present invention provides a composition for use in preventing or treating an eye condition, disorder, or disease, comprising an mTOR inhibitor. In particular, the mTOR inhibitor is effective against a condition, disorder, or disease in corneal endothelia.

Although an mTOR is understood to be involved in signaling inside a cell and is responsible for adjustment of cell mitosis, survival of a cell and the like, the mechanism thereof in corneal endothelia is not elucidated. Thus, it was unexpected and surprising that an mTOR inhibitor is effective in treating and preventing an ophthalmic, especially corneal endothelial, diseases, disorders, or conditions.

In one embodiment, a corneal endothelial condition, disorder, or disease due to transforming growth factor-β (TGF-β) in corneal endothelial cells is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

In still another preferred embodiment, the present invention provides a medicament having an action and effect for treating or preventing a condition due to overexpression of extracellular matrix in Fuchs' endothelial corneal dystrophy for use in treating or preventing such a condition, or a method of treating or preventing such a condition. Examples of such a condition include guttata on a corneal endothelial surface, turbid guttae of a Descemet's membrane, hypertrophy of the Descemet's membrane, blurred vision, halo, glare, reduced vision, corneal turbidity, leucoma, abnormality in visual sense, and the like. Conditions due to overproduction of extracellular matrix are further discussed below.

In still another aspect, the present invention provides a medicament for use in treating or preventing a corneal endothelial condition, disorder, or disease due to overexpression of extracellular matrix in corneal endothelial cells, comprising an mTOR inhibitor. As discussed above, an mTOR inhibitor can treat or prevent a corneal endothelial disorder or the like due to a TGF-β signal, but it was surprising that an mTOR inhibitor can also suppress overexpression of extracellular matrix in corneal endothelial cells. This suggests that an mTOR inhibitor can simultaneously treat corneal endothelial disorders due to a TGF-β signal and overexpression of extracellular matrix in corneal endothelial cells. In particular, Fuchs' endothelial corneal dystrophy is a disease in which the density of corneal endothelial cells significantly decreases due to a TGF-β signal, and extracellular matrix is deposited in the Descemet's membrane, resulting in corneal guttae and hypertrophy of the Descemet's membrane. For this reason, suppression of the overexpression of extracellular matrix means that therapy and prophylaxis of Fuchs' endothelial corneal dystrophy can be significantly improved, and is capable of complete healing in some cases. It is also possible to improve, treat, or prevent corneal guttae and hypertrophy of the Descemet's membrane, as well as other conditions associated with turbidity or deposition (irreversible turbidity in corneal stroma due to protracted corneal edema or the like) that can occur due to overproduction of extracellular matrix in corneal endothelial disorders such as Fuchs' endothelial corneal dystrophy.

In one embodiment, a corneal endothelial condition, disorder, or disease due to overexpression of extracellular matrix in corneal endothelial cells can be due to overexpression of fibronectin in corneal endothelial cells.

In one embodiment, a corneal endothelial condition, disorder, or disease due to overexpression of extracellular matrix in corneal endothelial cells is selected from the group consisting of Fuchs' endothelial corneal dystrophy, guttae formation, hypertrophy of the Descemet's membrane, hypertrophy of a cornea, turbidity, scar, turbidity in corneal stroma, corneal epithelial edema, corneal epithelial disorder, photophobia, and blurred vision.

In another aspect, the present invention provides a medicament for use in treating or preventing a corneal endothelial condition, disorder, or disease due to a TGF-β signal and overexpression of extracellular matrix in corneal endothelial cells, comprising an mTOR inhibitor. An mTOR inhibitor can simultaneously treat or prevent corneal endothelial disorders due to a TGF-β signal and overexpression of extracellular matrix in corneal endothelial cells.

In one embodiment, a corneal endothelial condition, disorder, or disease due to a TGF-β signal and overexpression of extracellular matrix in corneal endothelial cells is selected from the group consisting of Fuchs' endothelial corneal dystrophy, other endothelial corneal dystrophy, and a corneal endothelial disorder due to a drug, surgery, trauma, infection, uveitis, or the like.

In one embodiment, a corneal endothelial condition, disorder, or disease due to a TGF-β signal and overexpression of extracellular matrix in corneal endothelial cells comprises Fuchs' endothelial corneal dystrophy. Fuchs' endothelial corneal dystrophy is a disease in which the density of corneal endothelial cells significantly decreases due to a TGF-β signal and extracellular matrix is deposited in the Descemet's membrane, resulting in a disorder such as corneal guttae and hypertrophy of the Descemet's membrane. For this reason, suppression of the overexpression of extracellular matrix means that therapy can significantly improve Fuchs' endothelial corneal dystrophy, and complete healing in some cases. Improvement of a disorder or the like such as corneal guttae and hypertrophy of the Descemet's membrane in Fuchs' endothelial corneal dystrophy using an mTOR inhibitor causes qualitative improvement in an ophthalmic disease and provides an unconventional therapeutic effect against a disease such as Fuchs' endothelial corneal dystrophy which was beyond saving.

In one embodiment, examples of utilization methods of the present invention include, but are not limited to, eye drops, as well as administration methods such as injection into the anterior chamber, impregnation into a controlled-release agent, subconjunctival injection, and systemic administration (oral administration and intravenous injection).

In one embodiment, the mTOR inhibitor used in the present invention can be any type of mTOR inhibitor, as long as it is effective in treating or preventing a given eye (e.g., corneal endothelial) condition, disorder, or disease. Specific mTOR inhibitors include at least one selected from the group consisting of rapamycin, temsirolimus, everolimus, PI-103, CC-223, INK128, AZD8055, KU 0063794, Voxtalisib (XL765, SAR245409), Ridaforolimus (Deforolimus, MK-8669), NVP-BEZ235, CZ415, Torkinib (PP242), Torin 1, Omipalisib (GSK2126458, GSK458), OSI-027, PF-04691502, Apitolisib (GDC-0980, RG7422), WYE-354, Vistusertib (AZD2014), Torin 2, Tacrolimus (FK506), GSK1059615, Gedatolisib (PF-05212384, PKI-587), WYE-125132 (WYE-132), BGT226 (NVP-BGT226), Palomid 529 (P529), PP121, WYE-687, CH5132799, WAY-600, ETP-46464, GDC-0349, XL388, Zotarolimus (ABT-578), and Chrysophanic Acid.

The above mTOR inhibitors may be used alone or in combination in the medicament of the present invention. The concentration of an mTOR inhibitor used in the present invention can be appropriately changed in accordance with the type of the mTOR inhibitor. For example, the concentration can be, but is not limited to, at least about 0.0001 nM (nmol/L), at least about 0.001 nM, at least about 0.01 nM, at least about 0.1 nM, at least about 1 nM, at least about 10 nM, at least about 100 nM, or at least about 1000 nM. The upper limit of the concentration of an mTOR used in the present invention includes, but is not limited to, about 100 µM (µmol/L), about 10 µM, about 1 µM, or about 0.5 µM. Examples of the concentration rage of an mTOR inhibitor used in the present invention include, but are not limited to, about 0.01 nM to about 100 µM, about 0.1 nM to about 100 µM, about 1 nM to about 100 µM, about 10 nM to about 100 µM, about 100 nM to about 100 µM, about 1 µM to about 100 µM, about 0.01 nM to about 10 µM, about 0.1 nM to about 10 µM, about 1 nM to about 10 µM, about 10 nM to about 10 µM, about 100 nM to about 10 µM, about 1 µM to about 10 µM, about 0.01 nM to about 1 µM, about 0.1 nM to about 1 µM, about 1 nM to about 1 µM, about 10 nM to about 1 µM, about 100 nM to about 1 µM, about 0.01 nM to about 100 nM, about 0.1 nM to about 100 nM, about 1 nM to about 100 nM, and about 10 nM to about 100 nM. When two or more types of mTOR inhibitors are used in combination, the concentration of each mTOR inhibitor can be appropriately changed.

In a preferred embodiment, an mTOR inhibitor is selected from the group consisting of, for example, rapamycin, temsirolimus, everolimus, and salts thereof. Although not wishing to be bound by any theory, this is because it was found that treatment with mTOR inhibitors such as rapamycin, temsirolimus and everolimus exhibited a significantly better therapeutic result compared to other mTOR inhibitors, and results of healing especially a corneal endothelial disease or disorder associated with transforming growth factor-β2 (TGF-β2) such as Fuchs' endothelial dystrophy, or corneal endothelial disease or disorder associated with overexpression of extracellular matrix (ECM) are significantly improved. In addition, this is because these mTOR inhibitors are already approved by the FDA, PMDA and the like, and are expected to be able to be administered as an ophthalmic medicament as a pharmaceutical product even in view of aspects such as safety.

The above compounds may be used alone or in combination in the medicament of the present invention. The concentration of a compound used in the present invention is about 0.01 nM to 100 µM (µmol/1), or about 0.1 nM to 100 µm, generally about 1 nM to 100 µM, about 10 nM to 100 µM, preferably about 0.1 to 30 µM, and more preferably about 1 to 10 µM. The upper limits and lower limits thereof can be appropriately set in combination and when two or more types of compounds are used in combination, the concentration can be appropriately changed. Examples of other concentration ranges include, but are not limited to, generally about 0.01 nM to 100 µM, about 0.1 nM to 100 µM, or about 0.001 to 100 µM, preferably about 0.01 to 75 µM, about 0.05 to 50 µM, about 1 to 10 µM, about 0.01 to 10 µM, about 0.05 to 10 µM, about 0.075 to 10 µM, about 0.1 to 10 µM, about 0.5 to 10 µM, about 0.75 to 10 µM, about 1.0 to 10 µM, about 1.25 to 10 µM, about 1.5 to 10 µM, about 1.75 to 10 µM, about 2.0 to 10 µM, about 2.5 to 10 µM, about 3.0 to 10 µM, about 4.0 to 10 µM, about 5.0 to 10 µM, about 6.0 to 10 µM, about 7.0 to 10 µM, about 8.0 to 10 µM, about 9.0 to 10 µM, about 0.01 to 50 µM, about 0.05 to 5.0 µM, about 0.075 to 5.0 µM, about 0.1 to 5.0 µM, about 0.5 to 5.0 µM, about 0.75 to 5.0 µM, about 1.0 to 5.0 µM, about 1.25 to 5.0 µM, about 1.5 to 5.0 µM, about 1.75 to 5.0 µM, about 2.0 to 5.0 µM, about 2.5 to 5.0 µM, about 3.0 to 5.0 µM, about 4.0 to 5.0 µM, about 0.01 to 3.0 µM, about 0.05 to 3.0 µM, about 0.075 to 3.0 µM, about 0.1 to 3.0 µM, about 0.5 to 3.0 µM, about 0.75 to 3.0 µM, about 1.0 to 3.0 µM, about 1.25 to 3.0 µM, about 1.5 to 3.0 µM, about 1.75 to 3.0 µM, about 2.0 to 3.0 µM, about 0.01 to 1.0 µM, about 0.05 to 1.0 µM, about 0.075 to 1.0 µM, about 0.1 to 1.0 µM, about 0.5 to 1.0 µM, about 0.75 to 1.0 µM, about 0.09 to 35 µM, about 0.09 to 3.2 µM, more preferably about 0.05 to 1.0 µM, about 0.075 to 1.0 µM, about 0.1 to 1.0 µM, about 0.5 to 1.0 µM, about 0.75 to 1.0 µM.

When used as an eye drop, the formulation concentration can be determined using about 1 to 10000-fold, preferably about 100 to 10000-fold such as about 1000-fold of the above effective concentration as a reference while considering dilution with tear fluid or the like and paying attention to toxicity. It is also possible to set a higher concentration. For example, the concentration is about 0.01 µM (µMol/l) to 1000 mM (mmol/l), about 0.1 µM to 100 mM, about 1 µM to 100 mM, about 10 µM to 100 mM, or about 0.1 µM to 30 mM, about 1 µM to 30 mM, more preferably about 1 µM to 10 mM, about 10 µM to 10 mM, about 100 µM to 10 mM, about 10 µM to 100 mM, about 100 µM to 100 mM, or can be about ¥ mM to 10 mM, about 1 mM to 100 mM. The upper limits and lower limits thereof can be appropriately set in combination and when two or more types of compounds are used in combination, the concentration can be appropriately changed.

In another embodiment, an mTOR inhibitor is rapamycin. The concentration of the rapamycin to be used is at least about 0.1 nM, at least about 1 nM, at least about 10 nM, preferably about 100 nM. In a preferable embodiment, rapamycin is used as an eye drop and the concentration of the rapamycin to be used upon doing so is at least about 0.1 mM, at least about 1 mM, at least about 10 mM, preferably at least about 100 mM. Saturation amount or 1000 mM is exemplified as the upper limit of the concentration.

In another embodiment, an mTOR inhibitor is temsirolimus. The concentration of the temsirolimus to be used is at least about 0.01 nM, at least about 0.1 nM, preferably about 1 nM, preferably about 10 nM, more preferably about 100 nM, more preferably about 1 µM, more preferably about 10 µM. Temsirolimus is used as an eye drop and the concentration of the temsirolimus to be used upon doing so is at least about 0.01 mM, at least about 0.1 mM, at least about 1 mM, preferably at least about 10 mM. Saturation amount or 1000 mM is exemplified as the upper limit of the concentration. In another embodiment, an mTOR inhibitor is everolimus. The concentration of the everolimus to be used is at least about 0.1 nM, at least about 1 nM, at least about 10 nM, preferably about 100 nM. Everolimus is used as an eye drop and the concentration of the everolimus to be used upon doing so is at least about 0.1 mM, at least about 1 mM, at least about 10 mM, preferably at least about 100 mM. Saturation amount or 1000 mM is exemplified as the upper limit of the concentration.

In one embodiment, a therapeutic or prophylactic medicament of the present invention can be targeted for any animal with a corneal endothelium, such as mammals. Such a medicament is preferably intended for treating or preventing a primate corneal endothelium. The subject of therapy or prophylaxis is preferably a human corneal endothelium.

In still another embodiment, an mTOR inhibitor may be an mTOR gene expression suppressing substance. Examples of an mTOR gene expression suppressing substance include, but are not limited to, siRNA, antisense nucleic acid, or ribozyme.

In a specific embodiment, an mTOR inhibitor is an siRNA against an mTOR gene. Typical examples of siRNA used in the present invention include, but are not limited to:
a sense strand set forth in CAUUCGCAUUCAGUC-CAUAtt (SEQ ID NO: 1); and
an antisense strand set forth in UAUGGACUGAAUGCGAAUGat (SEQ ID NO: 2).
Any sequence is acceptable as long as there is an antisense effect or a sense RNAi effect against an mTOR gene. 1 to 3 bases of nucleotides may be deleted, substituted, inserted and/or added in these sense strand and antisense strands.

In another aspect, the present invention provides a method of treating or preventing an eye (e.g., corneal endothelial) condition, disorder, or disease (corneal endothelial condition, disorder, or disease due to a TGF-β signal and/or overexpression of extracellular matrix in corneal endothelial cells), comprising administering an effective amount of an mTOR inhibitor to a subject in need thereof.

As used herein, a "subject" refers to a target of administration (transplant) of a therapeutic or prophylactic medicament or method of the present invention. Examples of subjects include mammals (e.g., human, mouse, rat, hamster, rabbit, cat, dog, cow, horse, sheep, monkey and the like), but primates are preferable and humans are especially preferable.

The effective amount of the medicament of the present invention, which is effective in treating a specific disease, disorder, or condition, can vary depending on the properties of a disorder or condition, but the effective amount can be determined by those skilled in the art with standard clinical techniques based on the descriptions in the present specification. It is also possible to use an in vitro assay to assist in identifying the optimal range of dosage as needed. Since an accurate dose to be used in a formulation can vary depending on the route of administration and the severity of a disease or disorder, the dose should be determined in accordance with the judgment of a physician and the condition of each patient. However, the dosage, while not particularly limited, may be, for example, 0.001, 1, 5, 10, 15, 100, or 1000 mg/kg body weight or a value between any two such values per dose. The interval of administration, while not particularly limited, may be for example one or two doses for every 1, 7, 14, 21, or 28 days, or one or two doses for a number of days between any two such values. The dosage, number of doses, administration interval, and administration method may be appropriately selected depending on the age or body weight of a patient, condition, dosage form, target organ, or the like. For example, the present invention can be used as an eye drop. The medicament of the present invention can also be injected into the anterior chamber. A therapeutic drug preferably comprises a therapeutically effective amount or an effective amount of active ingredients at which a desired action is exerted. It may be determined that there is a therapeutic effect when a therapeutic marker significantly decreases after administration. The effective amount can be estimated from a dose-response curve obtained from an in vitro or animal model testing system.

<Preservation and Growth of Corneal Endothelial Cells>

In another aspect, the present invention provides a composition for preserving corneal endothelial cells, comprising an mTOR inhibitor. The present invention also provides a method for preserving corneal endothelial cells, encompassing contacting an effective amount of an mTOR inhibitor with corneal endothelial cells. It is understood that an embodiment of an mTOR inhibitor or the like used for preservation of corneal endothelial cells can use any embodiment described in the <Medicament> in the present specification. Contact to corneal endothelial cells can be performed in vivo, ex vivo, or in vitro, and can be used in the manufacturing of a cell formulation.

In another aspect, the present invention provides a composition for growing or promoting the growth of corneal endothelial cells, comprising an mTOR inhibitor. The present invention also provides a method for growing or promoting the growth of corneal endothelial cells, encompassing contacting an effective amount of an mTOR inhibitor with corneal endothelial cells. It is understood that an embodiment of an mTOR inhibitor or the like used for growing or promoting the growth of corneal endothelial cells can use any embodiment described in the <Medicament> in the present specification. Contact to corneal endothelial cells can be performed in vivo, ex vivo, or in vitro, and can be used in the manufacturing of a cell formulation.

Reference literature such as scientific literature, patents, and patent applications cited herein is incorporated herein by reference to the same extent that the entirety of each document is specifically described.

The present invention has been explained while showing preferred embodiments to facilitate understanding. The present invention is explained hereinafter based on Examples. The above explanation and the following Examples are not provided to limit the present invention, but for the sole purpose of exemplification. Thus, the scope of the present invention is not limited to the embodiments and Examples that are specifically disclosed herein and is limited only by the scope of claims.

EXAMPLES

Hereinafter, examples of the present invention are described. Biological samples or the like, where applicable, were handled in compliance with the standards enacted by the Ministry of Health, Labour and Welfare, Ministry of Education, Culture, Sports, Science and Technology, or the like and, where applicable, based on the Helsinki Declaration or ethical codes prepared based thereon. For the donation of eyes used for the study, consent was obtained from close relatives of all deceased donors. The present study was approved by the ethics committee or a corresponding body of the University of Erlangen-Nuremberg (Germany) and SightLife™ (Seattle, Wash.) eye bank.

Preparation Example: Production of Fuchs' Endothelial Corneal Dystrophy Patient Derived Immortalized Corneal Endothelial Cell Line (iFECD) Model In the present example, an immortalized corneal endothelial cell line (iFECD) was made from corneal endothelial cells from Fuchs' endothelial corneal dystrophy patients.

(Culture Method)

Corneal endothelial cells were mechanically peeled off with a basal membrane from a cornea for research purchased from the Seattle Eye Bank. After using collagenase to detach and collect the corneal endothelial cell from the basal membrane, the cells were subjected to primary culture. For the medium, Opti-MEM I Reduced-Serum Medium, Liquid (INVITROGEN catalog number: 31985-070), to which 8% FBS (BIOWEST, catalog number: S1820-500), 200 mg/mL of $CaCl_2 \cdot 2H_2O$ (SIGMA catalog number: C7902-500G), 0.08% of chondroitin sulfate (SIGMA catalog number: C9819-5G), 20 µg/mL of ascorbic acid (SIGMA catalog number: A4544-25G), 50 µg/mL of gentamicin (INVITROGEN catalog number: 15710-064) and 5 ng/mL of EGF (INVITROGEN catalog number: PHG0311) were added, and conditioned for a 3T3 feeder cell was used as a basal medium. Further, the cells were cultured in a basal medium to which SB431542 (1 µmol/L) and SB203580 (4-(4-fluorophenyl)-2-(4-methylsulfonylphenyl)-5(4-pyridyl) imidazole<4-[4-(4-fluorphenyl)-2-(4-methylsulfinylphenyl)-1H-imidazole-5-yl]pyridine) (1 µmol/L) were added (also referred to as "SB203580+SB431542+3T3 conditioned medium" herein).

(Method of Acquisition)

Corneal endothelial cells were obtained with approval from an ethics committee and written consent from 3 human patients who suffered from bullous keratopathy according to a clinical diagnosis of Fuchs' endothelial corneal dystrophy and underwent corneal endothelial transplant (Descemet's Membrane Endothelial Keratoplasty=DMEK). For DMEK, pathological corneal endothelial cells were mechanically peeled off with the basal membrane, i.e., the Descemet's membrane, and immersed in a cornea preservation solution Optisol-GS (Bausch & Lomb). Collagenase treatment was then applied to enzymatically collect the corneal endothelial cells, and the cells were cultured with a SB203580+ SB431542+3T3 conditioned medium. For cultured corneal endothelial cells from a Fuchs' endothelial corneal dystrophy patient, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) with a transfection reagent (Fugene HD; Promega Corp., Madison, Wis.) and three types of helper plasmids (pLP1, pLP2, pLP/VSVG; Life Technologies Inc.). Culture supernatant comprising viruses was collected after 48 hours from the infection. 5 µg/ml of polybrene was used and added to a culture solution of cultured corneal endothelial cells from a Fuchs' endothelial corneal dystrophy patient, and SV40 large T antigen and hTERT gene were introduced. Images of immortalized corneal endothelial cell line (iFECD) from Fuchs' endothelial corneal dystrophy patients from a phase difference microscope were studied. Cultured corneal endothelial cells from a research cornea imported from the Seattle Eye Bank were immortalized by the same method to make an immortalized cell line of normal corneal endothelial cells (iHCEC) as a control. When images of the immortalized corneal endothelial cell line (iFECD) and the immortalized corneal endothelial cell line from a healthy donor (iHCEC) from a phase difference microscope are studied, both iHCEC and iFECD have a layer of polygonal form as in normal corneal endothelial cells. IHCEC and iFECD were maintained and cultured with Dulbecco's Modified Eagle Medium (DMEM)+10% fetal bovine serum (FBS).

Example 1: Suppression Effect of Rapamycin on Cell Damage Induced by TGF-β2

This Example demonstrated the effect of rapamycin, which is a typical example of an mTOR inhibitor, on cell damage.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of 1×10$^5$ cells per well and cultured for 24 hours at 37° C. (5% $CO_2$) (DMEM+10% FBS+1% P/S was used as the medium). After 24 hours, the medium was removed. Rapamycin was added to culture the cells for 24 hours. (DMEM+2% FBS+1% P/S was used as the medium). After 24 hours, the medium was removed. A medium containing 10 ng/ml of Recombinant Human TGF-β2 (Wako, 200-19911) and rapamycin was added to culture the cells for 24 hours. (DMEM+2% FBS+1% P/S was used as the medium). After 24 hours, the cell morphology and apoptosis were observed under a phase contrast microscope.

(Results)

(Rapamycin Suppresses Cell Damage Induced by TGF-β2)

FIG. 1 shows the results. When iFECDs were stimulated with Recombinant Human TGF-β2 in the absence of rapamycin, cells were found to be significantly damaged. On the other hand, it was observed that damage to corneal endothelial cells was suppressed when pretreated with rapamycin. Therefore, rapamycin was found to suppress cell damage induced by Recombinant Human TGF-β2.

Example 2: Suppression Effect of Rapamycin on Caspase Activity Induced by TGF-β2

This Example demonstrated the effect of rapamycin, which is a typical example of an mTOR inhibitor, on caspase activity.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of 1×10$^5$ cells per well and cultured for 24 hours at 37° C. (5% $CO_2$) (DMEM+10% FBS+1% P/S was used as the medium). After 24 hours, the medium was removed. Rapamycin was added to culture the cells for 24 hours. (DMEM+2% FBS+1% P/S was used as the medium). After 24 hours, the medium was removed. A medium containing 10 ng/ml of Recombinant Human TGF-β2 (Wako, 200-19911) and rapamycin was added to culture the cells for 24 hours. (DMEM+2% FBS+1% P/S was used as the medium). After 24 hours, the cell morphology and apoptosis were observed under a phase contrast microscope.

After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

8 µg of the extracted protein was separated by SDS-PAGE and transferred onto a nitrocellulose membrane. A rabbit anti-Caspase 3 antibody (Cell Signaling, 9662), rabbit anti-PARP antibody (Cell Signaling, 9542), and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, rabbit anti-Caspase 3 antibody: 1000-fold dilution, rabbit anti-PARP antibody: 2000-fold dilution, and mouse anti-GAPDH antibody: 5000-fold dilution, while the secondary antibody was diluted 5000-fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

(Rapamycin Suppresses Caspase Activity Induced by TGF-β2)

The results of western blot of caspase are shown in FIG. 2. When iFECDs were stimulated with Recombinant Human TGF-β2 in the absence of rapamycin, cleaved caspase 3 (about 17 kDa), which is an active form, was observed. On the other hand, activated form of cleaved caspase 3 was hardly observed in the rapamycin supplemented group. Therefore, caspase activation by Recombinant Human TGF-β2 was found to be suppressed by rapamycin in the analysis. An mTOR is not related to caspase signal and it is not known that an mTOR inhibitor suppresses caspase activity. Thus, it was surprising that rapamycin was able to suppress caspase activity.

Example 3: Suppression Effect of Rapamycin on Phosphorylation Activity of S6K Induced by Recombinant Human TGF-β2

This Example demonstrated the effect of rapamycin, which is a typical example of an mTOR inhibitor, on phosphorylation activity of S6K induced by Recombinant Human TGF-β2.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of $7\times10^4$ cells per well and cultured for 24 hours at 37° C. (5% $CO_2$) (DMEM+10% FBS+1% P/S was used as the medium). After 24 hours, the medium was removed. Rapamycin was added to culture the cells for 24 hours. (DMEM+2% FBS+1% P/S was used as the medium). After 24 hours, the medium was removed. A medium containing 10 ng/ml of Recombinant Human TGF-β2 (Wako, 200-19911) and rapamycin was added to culture the cells for 24 hours. (DMEM+2% FBS+1% P/S was used as the medium). After 24 hours, the cell morphology and apoptosis were observed under a phase contrast microscope.

After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

8 μg of the extracted protein was separated by SDS-PAGE and transferred onto a nitrocellulose membrane. A rabbit anti-Akt1 antibody (Cell Signaling, 2938), mouse anti-Phospho-Akt antibody (Cell Signaling, 4051), rabbit anti-S6K antibody (Cell Signaling, 9202), rabbit anti-Phospho-S6K antibody (Cell Signaling, 9204) and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, rabbit anti-Akt antibody: 1000-fold dilution, mouse anti-Phospho-Akt antibody: 1000-fold dilution, rabbit anti-S6K antibody: 1000-fold dilution, rabbit anti-Phospho-S6K antibody: 1000-fold dilution, and mouse anti-GAPDH antibody: 5000-fold dilution, while the secondary antibody was diluted 5000-fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

(Rapamycin Suppresses Phosphorylation Activity of S6K induced by TGF-β2)

Figure 3:
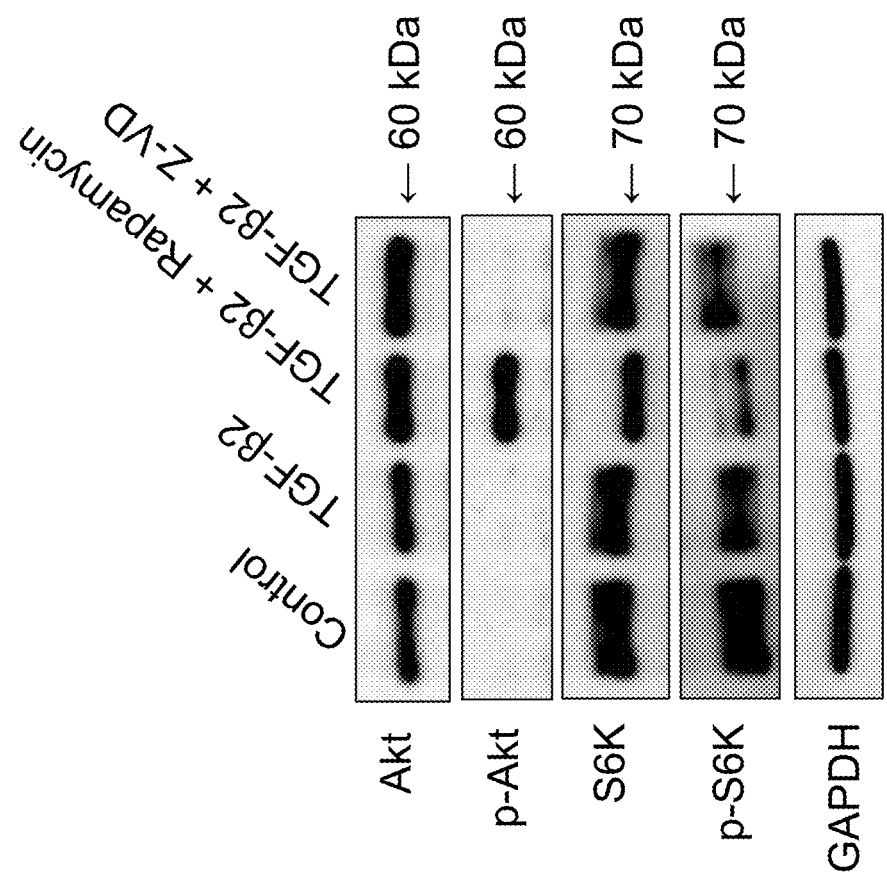
FIG. 3 shows the results of western blot on Akt, p-Akt, S6K, p-S6K, and GAPDH. The figure shows, from the left, a control group wherein TGF-β2 is not supplemented, a group wherein TGF-β2 is supplemented, a group wherein TGF-β2 and rapamycin are supplemented, and a group wherein TGF-β2 and Z-VD-FMK, which is a caspase inhibitor, are supplemented.

The results are shown in FIG. 3. When iFECDs were stimulated with Recombinant Human TGF-β2 in the absence of rapamycin, phosphorylation activity of Akt was found. On the other hand, phosphorylation activity of S6K was suppressed in the rapamycin supplemented group. Rapamycin was found to have mTOR signal pathway inhibitory action by western blot analysis in rapamycin. Akt is present upstream of mTOR and S6K is present downstream of mTOR. Thus, in view of the fact that the upstream Akt was phosphorylated while phosphorylation of the downstream S6K was suppressed by the mTOR inhibitor, rapamycin was found to be inhibiting an mTOR pathway.

Example 4: Suppression Effect of Rapamycin on Phosphorylation Activity of Smad2/3 Induced by TGF-β2

This Example demonstrated suppression effect of rapamycin, which is a typical example of an mTOR inhibitor, on phosphorylation activity of Smad2/3 induced by TGF-β2.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of $8 \times 10^4$ cells per well and cultured for 24 hours at 37° C. (5% $CO_2$) (DMEM+10% FBS+1% P/S was used as the medium). After 24 hours, the medium was removed. Rapamycin was added to culture the cells for 24 hours. (DMEM+2% FBS+1% P/S was used as the medium). After 24 hours, the medium was removed. A medium containing 10 ng/ml of Recombinant Human TGF-β2 (Wako, 200-19911) and rapamycin was added to culture the cells for 24 hours. (DMEM+2% FBS+1% P/S was used as the medium). After 24 hours, the cell morphology and apoptosis were observed under a phase contrast microscope.

After observation, western blot was performed on proteins by the following procedure.

1) Protein Collection

The Medium was Collected on Ice to Collect Free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

8 μg of the extracted protein was separated by SDS-PAGE and transferred onto a nitrocellulose membrane. A rabbit anti-Smad2 antibody (Cell Signaling, 5339), mouse anti-Phospho-Smad2 antibody (Cell Signaling, 3108), rabbit anti-Smad3 antibody (Cell Signaling, 9523), rabbit anti-Phospho-Smad3 antibody (Cell Signaling, 9520) and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, rabbit anti-Smad2 antibody: 1000-fold dilution, mouse anti-Phospho-Smad2 antibody: 1000-fold dilution, rabbit anti-Smad3 antibody: 1000-fold dilution, rabbit anti-Phospho-Smad3 antibody: 1000-fold dilution, and mouse anti-GAPDH antibody: 5000-fold dilution, while the secondary antibody was diluted 5000-fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

(Rapamycin does not Suppress Phosphorylation Activity of Smad2/3 Induced by TGF-β2)

Figure 4:
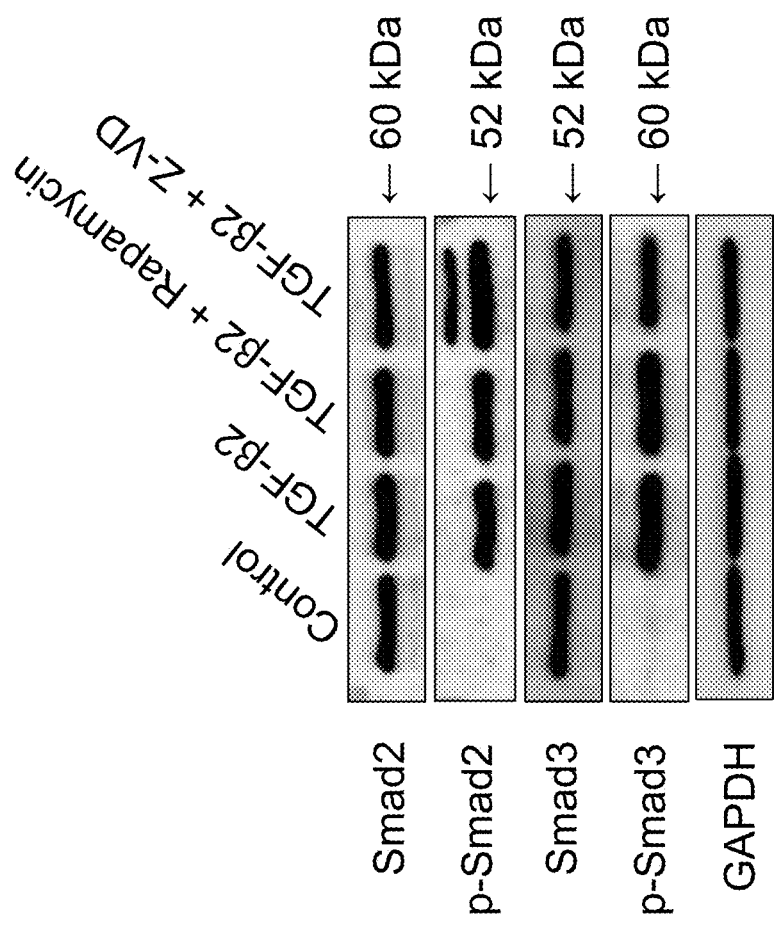
FIG. 4 shows the results of western blot on Smad2, p-Smad2, Smad3, p-Smad3, and GAPDH. The figure shows, from the left, a control group wherein TGF-β2 is not supplemented, a group wherein TGF-β2 is supplemented, a group wherein TGF-β2 and rapamycin are supplemented, and a group wherein TGF-β2 and Z-VD-FMK, which is a caspase inhibitor, are supplemented.

The results are shown in FIG. 4. When stimulated with Recombinant Human TGF-β2 in the absence of rapamycin, phosphorylation activities of Smad2 and Smad3 were found. Thus, phosphorylation activity of Smad2/3 induced by Recombinant Human TGF-β2 was found not to be suppressed by rapamycin in western blot analysis. It was revealed that cell damage suppression action of rapamycin is not due to inhibition of a TGF-β signal since the action of TGF-β is understood to be transmitted by a phosphorylation pathway of Smad. This suggests that rapamycin suppresses a corneal endothelial disorder and the like due to a TGF-β signal without directly inhibiting the TGF-β signal, which was an unexpected result.

Example 5: Suppression Effect of Rapamycin on Production of Fibronectin Induced by TGF-β2

This Example demonstrated suppression effect of rapamycin, which is a typical example of an mTOR inhibitor, on the production of fibronectin induced by TGF-β2.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 6-well plate at a ratio of $2 \times 10^5$ cells per well and cultured for 24 hours at 37° C. (5% $CO_2$) (DMEM+10% FBS+1% P/S was used as the medium). After 24 hours, the medium was removed. Rapamycin was added to culture the cells for 24 hours. (DMEM+2% FBS+1% P/S was used as the medium). After 24 hours, the medium was removed. A medium containing 10 ng/ml of Recombinant Human TGF-β2 (Wako, 200-19911) and rapamycin was added to culture the cells for 24 hours. (DMEM+2% FBS+1% P/S was used as the medium). After 24 hours, the cell morphology and apoptosis were observed under a phase contrast microscope.

After observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

5 μg of the extracted protein was separated by SDS-PAGE and transferred onto a nitrocellulose membrane. A mouse anti-Fibronectin antibody (BD Bioscience, 610077), and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the mouse anti-Fibronectin antibody: 15000-fold dilution and mouse anti-GAPDH antibody: 5000-fold dilution, while the secondary antibody was diluted 5000- fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

(Rapamycin Suppresses Production of Fibronectin Induced by TGF-β2)

Figure 5:
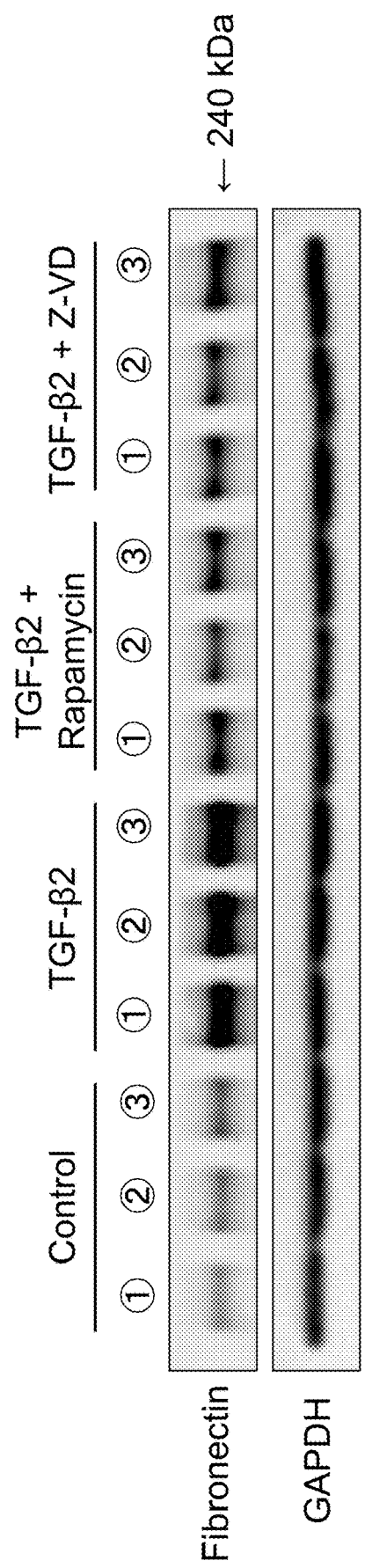
FIG. 5 shows the results of western blot on fibronectin and GAPDH (n=3). The figure shows, from the left, a control group wherein TGF-β2 is not supplemented, a group wherein TGF-β2 is supplemented, a group wherein TGF-β2 and rapamycin are supplemented, and a group wherein TGF-β2 and Z-VD-FMK, which is a caspase inhibitor, are supplemented.

The results are shown in FIG. 5. When stimulated with Recombinant Human TGF-β2 in the absence of rapamycin, production of fibronectin was observed in iFECD. On the other hand, production of fibronectin was hardly observed in the rapamycin supplemented group. Therefore, the amount of expression of fibronectin induced by Recombinant Human TGF-β2 was found to be suppressed by rapamycin in western blot analysis. It was not known that an mTOR inhibitor is involved in the production of extracellular matrix such as fibronectin. Thus, it was unexpected that an mTOR is able to suppress extracellular matrix production.

Figure 18:
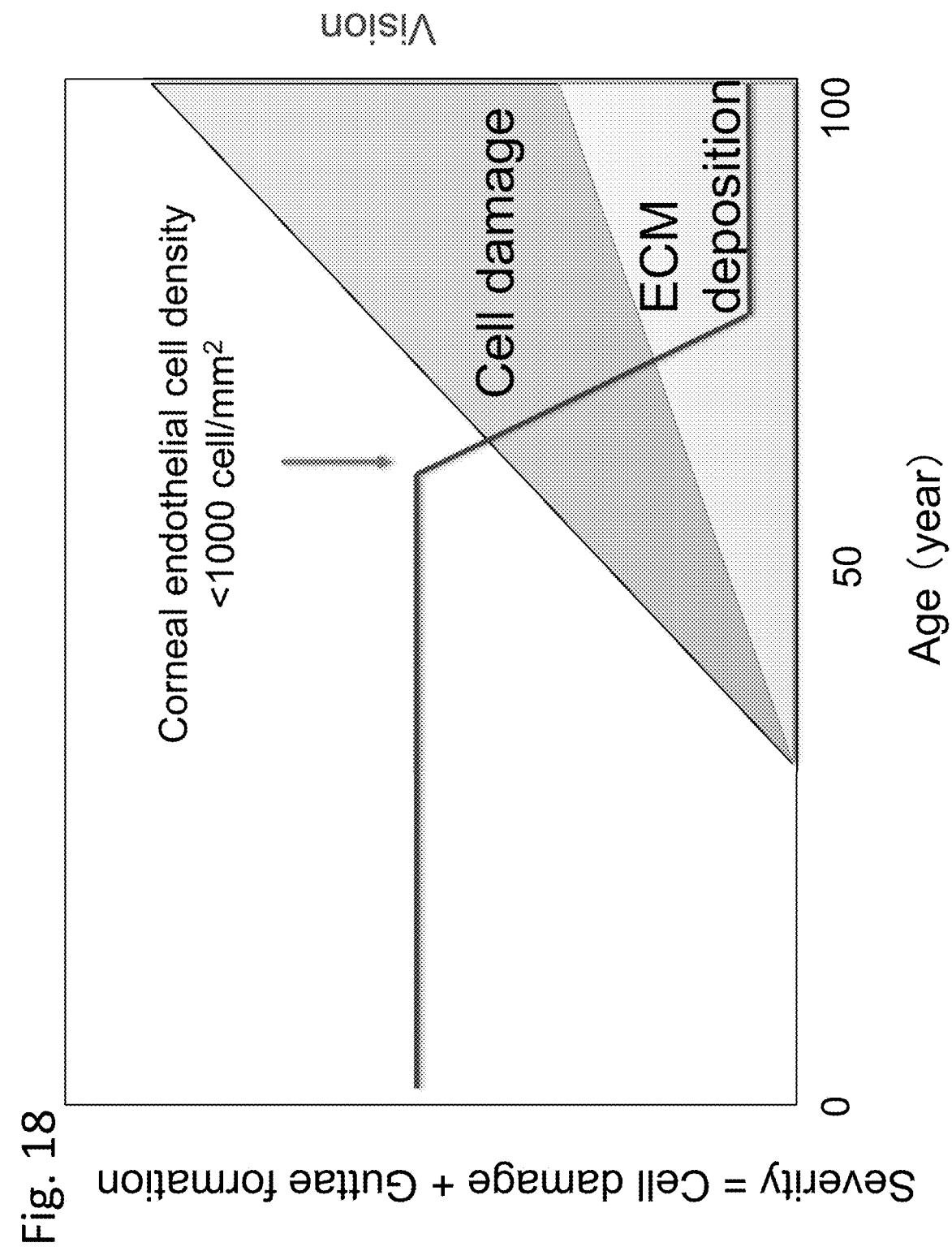
FIG. 18 shows a schematic diagram of the relationship of vision with corneal endothelial cells and ECM deposition. The diagram shows that vision deteriorates as corneal endothelial cells and ECM deposition increases. Hypertrophy of the Descemet's membrane or guttae due to ECM deposition commonly starts developing in the age of 30s and 40s in Fuchs' endothelial corneal dystrophy patients, and progresses throughout the patients' lives. Progression results in visual impairment such as blurred vision, halo, glare, or reduced vision. While corneal endothelial cell death progresses concurrently, the transparency of a corneal is maintained by the remaining corneal endothelia compensating for the pumping function until the corneal endothelial cell density is below about 1000 cells/mm$^2$. If the density is below about 1000 cells/mm$^2$, infiltration of the anterior aqueous humor into the cornea leads to corneal edema, resulting in severe visual impairment. The present technique can maintain visual function by suppressing both ECM deposition and corneal endothelial cell death.

In Fuchs' endothelial corneal dystrophy, overproduction of extracellular matrix such as fibronectin and deposition thereof on the Descemet's membrane result in a disorder such as hypertrophy of the Descemet's membrane or guttae formation. Such a disorder commonly starts developing in the 30s and 40s in Fuchs' endothelial corneal dystrophy patients, and progresses throughout the patient's life. Progression results in visual impairment such as blurred vision, halo, glare, or reduced vision. While corneal endothelial cells are continually damaged in Fuchs' endothelial corneal dystrophy, the transparency of the corneal is maintained by the remaining corneal endothelia compensating for the pumping function until the corneal endothelial cell density is below about 1000 cells/mm$^2$. If the density is below about 1000 cells/mm$^2$, infiltration of anterior aqueous humor into the cornea leads to corneal edema, resulting in visual impairment (FIG. 18). In this manner, Fuchs' endothelial corneal dystrophy patients suffer from a visual function disorder due to mainly two causes, i.e., overproduction of extracellular matrix and corneal endothelial cell death. The caspase inhibitor in the present invention have a role in both suppression of extracellular matrix production and suppression of corneal endothelial cell death to be especially useful in the therapy of Fuchs' endothelial corneal dystrophy.

Example 6: mTOR siRNA Suppression Effect on mTOR Expression and Phosphorylation of S6K This Example demonstrated the suppression effect of mTOR siRNA, which is another typical example of an mTOR inhibitor, on mTOR expression and phosphorylation of S6K.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of 3×10$^4$ cells per well and cultured for 24 hours at 37° C. (5% $CO_2$) (medium: DMEM+10% FBS+1% P/S). After 24 hours, the medium was removed. Lipofectamine (invitrogen, 92008) and 3 pmol of mTOR siRNA (Ambion, AS026M0L) were added to culture the cells for 24 hours (medium: OptiMEM-I (invitrogen, 31985-088)). The mTOR siRNA that was used has a sense strand set forth in SEQ ID NO: 1 and an antisense strand set forth in SEQ ID NO: 2. After 24 hours, the medium was removed to culture the cells for 72 hours at 37° C. (5% $CO_2$) (medium: DMEM+10% FBS+1% P/S). After 72 hours, the medium was removed. Media containing 10 ng/ml of Recombinant Human TGF-β2 (Wako, 200-19911) were added to culture the cells for 24 hours (medium: DMEM+2% FBS+1% P/S). After 24 hours, the cell morphology and apoptosis were observed under a phase difference microscope.

After observation, amplification of a base sequence of cDNA was carried out by PCR method with the following procedure.

1) Total RNA Collection

The medium was removed from a culture dish in which iFECDs were being cultured, and the cells were supplemented with 350 μl of Buffer RLT Lysis buffer of RNeasy miniKit (QIAGEN, M610A), and were eluted. The cells were supplemented with 350 μl of 70% EtOH and moved to RNeas mini spin column (QIAGEN) to then be centrifuged for 15 seconds at 10000 rpm to discard Flow-through. Furthermore, 30 μl of RNeasy free water (QIAGEN) was supplemented to RNeasy mini spin column to then carry out centrifugation for 1 minute at 10000 rpm to extract total RNA.

2) cDNA Synthesis

Each of the extracted total RNA 450 ng, Rever Tra Ace (TOYOBO), 10 mM dNTP Mixture (TOYOBO), 5×RT Buffer (TOYOBO) and random primer (invitrogen) were added to synthesize an complementary DNA using T3000 Thermocycler (biometra). The reaction condition was to carry out annealing reaction for 10 minutes at 30° C., reverse transcription reaction for 60 minutes at 42° C. and thermal denaturation reaction for 5 minutes at 99° C.

3) PCR Method

1 μl of the synthesized complementary DNA, 5 μl of 2×GO Taq GreenMaster Mix (Promega), 1 μl of Forward custom primer (invitrogen) of mTOR, 1 μl of Reverse custom primer (invitrogen) and 2 μl of $H_2O$ were mixed to amplify the base sequence of the complementary DNA using T3000 Thermocycler (biometra). The reaction condition was to carry out initial thermal denaturation reaction for 2 minutes at 94° C., followed by 26 cycles of thermal denaturation reaction for 30 seconds at 95° C., annealing reaction for 20 seconds at 53° C. and elongation reaction for 25 seconds at 72° C. Furthermore, elongation reaction was carried out for 5 minutes at 72° C. After the amplification, detection was carried out by UV irradiation with Amersham™ Imager 600 (GE Healthcare Japan) and electrophoresis using agarose gel.

Furthermore, after observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

5 μg of the extracted protein was separated by SDS-PAGE and transferred onto a nitrocellulose membrane. A rabbit anti-mTOR antibody (Cell Signaling, 2972), rabbit anti-S6K antibody (Cell Signaling, 9202), rabbit anti-Phospho-S6K antibody (CellSignaling, 9204), and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, rabbit anti-mTOR antibody: 1000-fold dilution, rabbit anti-S6K antibody: 1000-fold dilution, rabbit anti-Phospho-S6K antibody: 1000-fold dilution and mouse anti-GAPDH antibody: 5000-fold dilution, while the secondary antibody was diluted 5000-fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

(mTOR siRNA Suppresses mTOR Expression and Phosphorylation of S6K)

Figure 6:
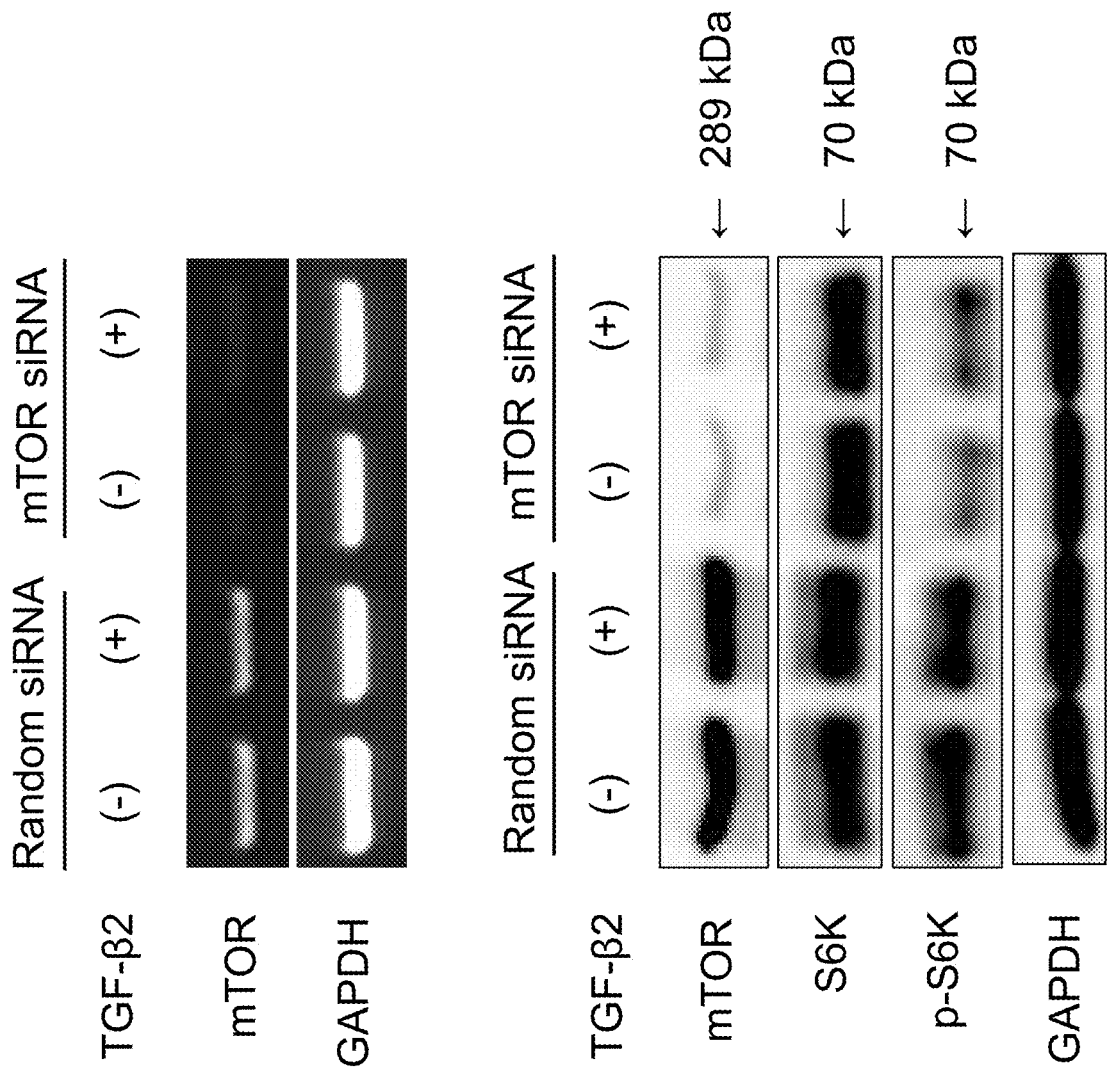
FIG. 6 shows the results of agarose gel electrophoresis and western blot. The top panel shows the result of the agarose gel electrophoresis on mTOR and GAPDH and the bottom panel shows the results of the western blot on mTOR, S6K, p-S6K, and GAPDH. The figure shows, from the left of each panel, a Random siRNA-supplemented group, a TGF-β2+Random siRNA-supplemented group, an mTOR siRNA-supplemented group, and a TGF-β2+mTOR siRNA-supplemented group.

The results are shown in FIG. 6. When RNAi is carried out against an mTOR in iFECD, mTOR expression suppression was found in both RNA level and protein level. In addition, phosphorylation of S6K was found to be suppressed in the protein level by mTOR siRNA. Thus, mTOR expression and phosphorylation of S6K were found to be suppressed by mTOR siRNA in PCR and western blot analyses.

Example 7: Suppression Effect of mTOR siRNA on Cell Damage Induced by TGF-β2

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of $3\times10^4$ cells per well and cultured for 24 hours at 37° C. (5% $CO_2$) (medium: DMEM+10% FBS+1% P/S). After 24 hours, the medium was removed. Lipofectamine (invitrogen, 92008) and 3 pmol of mTOR siRNA (Ambion, AS026M0L) were added to culture the cells for 24 hours (medium: OptiMEM-I (invitrogen, 31985-088)). The mTOR siRNA that was used has a sense strand set forth in SEQ ID NO: 1 and an antisense strand set forth in SEQ ID NO: 2. After 24 hours, the medium was removed to culture the cells for 72 hours at 37° C. (5% $CO_2$) (medium: DMEM+10% FBS+1% P/S). After 72 hours, the medium was removed. Media containing 10 ng/ml of Recombinant Human TGF-β2 (Wako, 200-19911) were added to culture the cells for 24 hours (medium: DMEM+2% FBS+1% P/S). After 24 hours, the cell morphology and apoptosis were observed under a phase difference microscope.

(Results)

(mTOR siRNA Suppresses Cell Damage Induced by TGF-β2)

Figure 7:
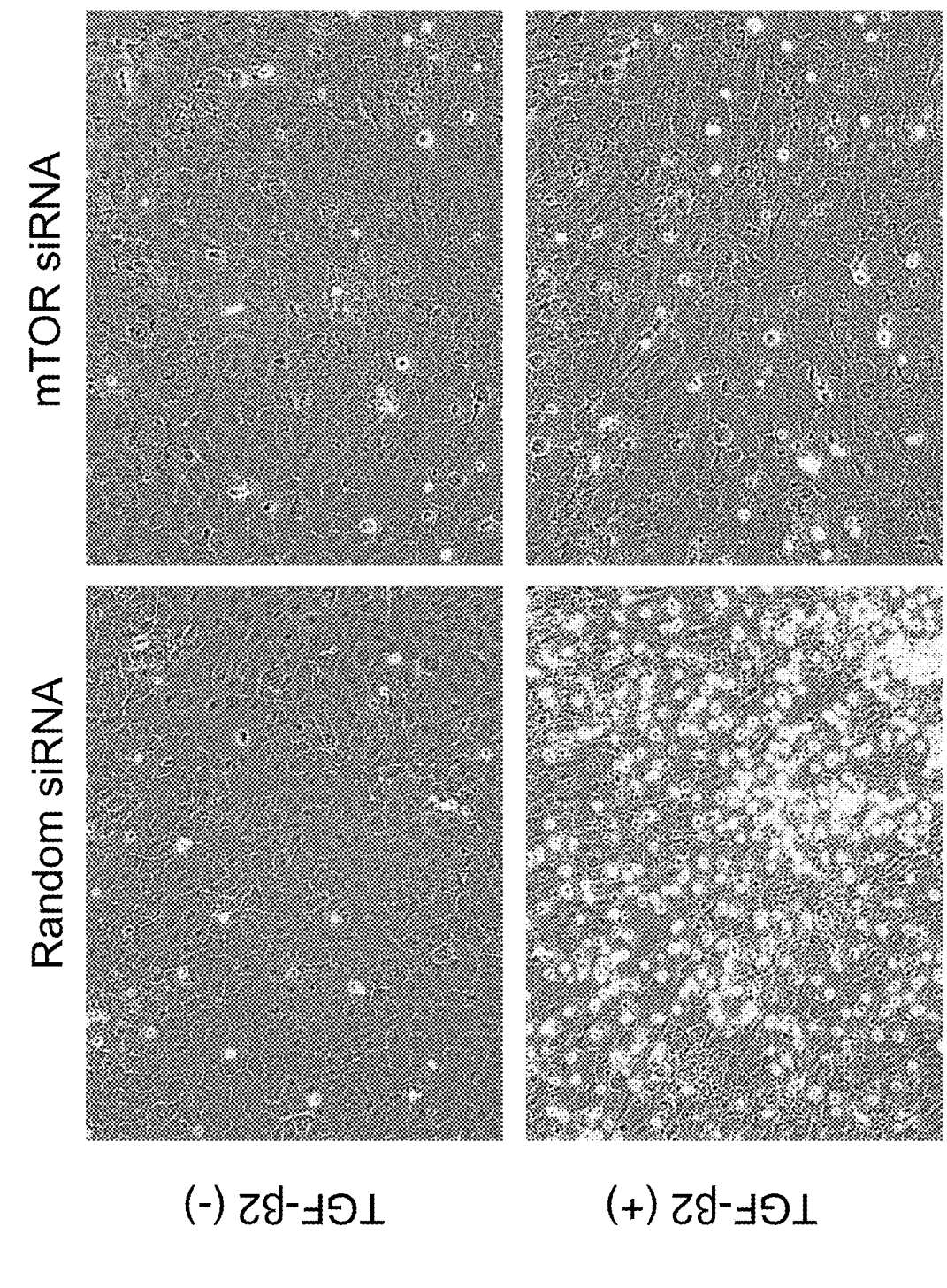
FIG. 7 shows microscopic images of iFECDs. The top left image shows a Random siRNA-supplemented group, the top right image shows an mTOR siRNA-supplemented group, the bottom left image shows a TGF-β2+Random siRNA-supplemented group, and the bottom right image shows a TGF-β2+mTOR siRNA-supplemented group.

The results are shown in FIG. 7. When iFECDs were stimulated with Recombinant Human TGF-β2 without using mTOR siRNA, cells were found to be significantly damaged. On the other hand, it was observed that damage to corneal endothelial cells was suppressed when mTOR siRNA was used. Therefore, mTOR expression suppression was found to suppress cell damage induced by TGF-β2.

Example 8: Suppression Effect of mTOR siRNA on Caspase Activation Induced by TGF-β2

This Example demonstrated the suppression effect of mTOR siRNA, which is another typical example of an mTOR inhibitor, on caspase activation induced by TGF-β2.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of $3\times10^4$ cells per well and cultured for 24 hours at 37° C. (5% $CO_2$) (medium: DMEM+10% FBS+1% P/S). After 24 hours, the medium was removed. Lipofectamine (invitrogen, 92008) and 3 pmol of mTOR siRNA (Ambion, AS026M0L) were added to culture the cells for 24 hours (medium: OptiMEM-I (invitrogen, 31985-088)). The mTOR siRNA that was used has a sense strand set forth in SEQ ID NO: 1 and an antisense strand set forth in SEQ ID NO: 2. After 24 hours, the medium was removed to culture the cells for 72 hours at 37° C. (5% $CO_2$) (medium: DMEM+10% FBS+1% P/S). After 72 hours, the medium was removed. Media containing 10 ng/ml of Recombinant Human TGF-β2 (Wako, 200-19911) were added to culture the cells for 24 hours (medium: DMEM+2% FBS+1% P/S). After 24 hours, the cell morphology and apoptosis were observed under a phase difference microscope.

Furthermore, after observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

6 μg of the extracted protein was separated by SDS-PAGE and transferred onto a nitrocellulose membrane. A rabbit anti-Caspase 3 antibody (Cell Signaling, 9662), rabbit anti-PARP antibody (Cell Signaling, 9542), and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, rabbit anti-Caspase 3 antibody: 1000-fold dilution, rabbit anti-PARP antibody: 2000-fold dilution and mouse anti-GAPDH antibody: 5000-fold dilution, while the secondary antibody was diluted 5000-fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

(mTOR siRNA Suppresses Caspase Activation Induced by TGF-β2)

Figure 8:
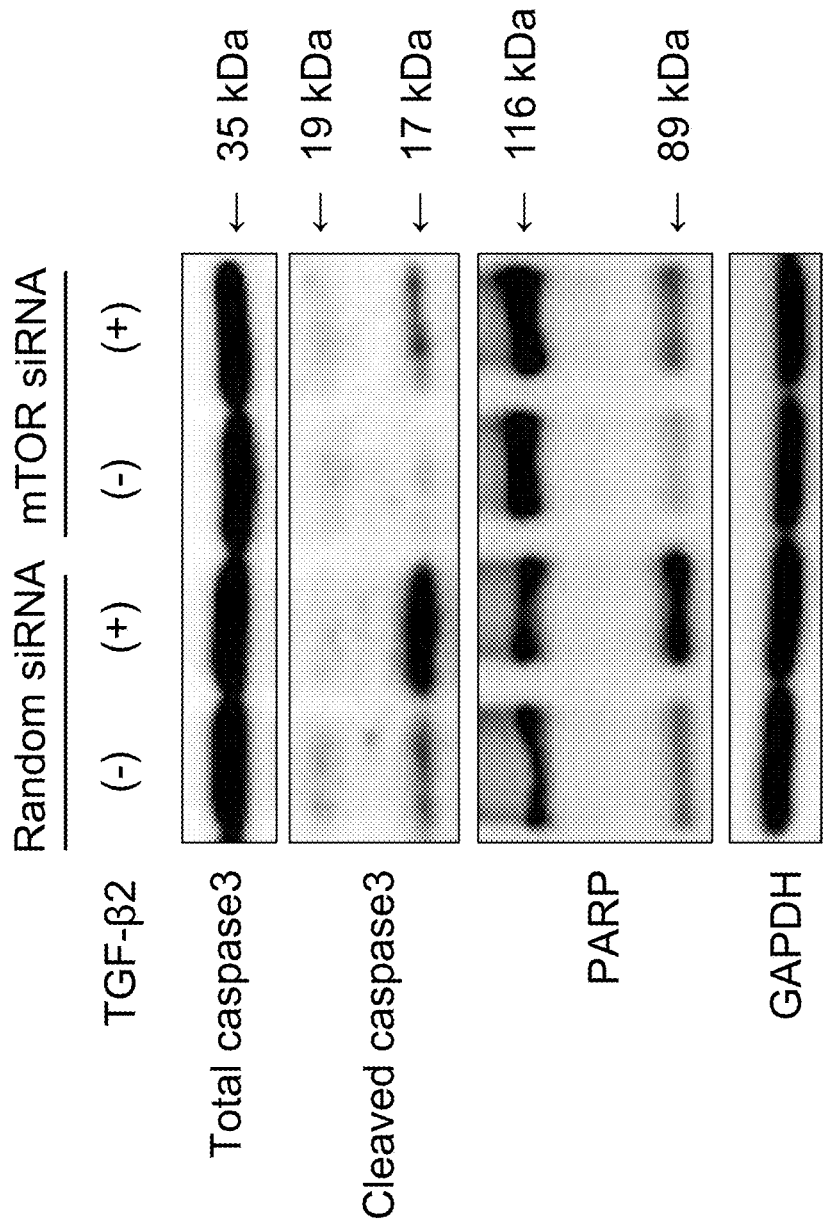
FIG. 8 shows the results of western blot on total caspase 3, cleaved caspase 3, PARP and GAPDH. The figure, from the left, shows a Random siRNA-supplemented group, a TGF-β2+Random siRNA-supplemented group, an mTOR siRNA-supplemented group, and a TGF-β2+mTOR siRNA-supplemented group.

The results are shown in FIG. 8. When iFECDs were stimulated with Recombinant Human TGF-β2 without using mTOR siRNA, about 17 kDa of cleaved caspase-3, which is an active form, was observed in iFECD. On the other hand, activated form of cleaved caspase-3 was hardly observed in the mTOR siRNA supplemented group. Thus, caspase activation induced by TGF-β2 was demonstrated to be suppressed by western blot analysis in mTOR signal suppression.

Example 9: Suppression Effect of mTOR siRNA on Production of Fibronectin Induced by TGF-β2

This Example demonstrated the suppression effect of mTOR siRNA, which is another typical example of an mTOR inhibitor, on production of fibronectin induced by TGF-β2

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium.

iFECDs were seeded on a 12-well plate at a ratio of $3×10^4$ cells per well and cultured for 24 hours at 37° C. (5% $CO_2$) (medium: DMEM+10% FBS+1% P/S). After 24 hours, the medium was removed. Lipofectamine (invitrogen, 92008) and 3 pmol of mTOR siRNA (Ambion, AS026M0L) were added to culture the cells for 24 hours (medium: OptiMEM-I (invitrogen, 31985-088)). The mTOR siRNA that was used has a sense strand set forth in SEQ ID NO: 1 and an antisense strand set forth in SEQ ID NO: 2. After 24 hours, the medium was removed to culture the cells for 48 hours at 37° C. (5% $CO_2$) (medium: DMEM+10% FBS+1% P/S). After 48 hours, the medium was removed. Media containing 10 ng/ml of Recombinant Human TGF-β2 (Wako, 200-19911) were added to culture the cells for 24 hours (medium: DMEM+2% FBS+1% P/S). After 24 hours, the cell morphology and apoptosis were observed under a phase difference microscope.

Furthermore, after observation, western blot was performed on proteins by the following procedure.

1) Protein Collection

The medium was collected on ice to collect free and dead cells. The solution from washing the cells twice with 1×PBS (−) was also collected. 800 g was centrifuged at 4° C. for 12 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIORUPTOR, TOSHO DENKI) and centrifuged for 10 min at 4° C. at 15000 rpm to collect the supernatant of proteins.

2) Western Blot

7 μg of the extracted protein was separated by SDS-PAGE and transferred onto a nitrocellulose membrane. A mouse anti-Fibronectin antibody (BDBioscience, 610077) and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, rabbit anti-Caspase 3 antibody: 1000-fold dilution, rabbit anti-PARP antibody: 2000-fold dilution, and mouse anti-GAPDH antibody: 5000-fold dilution, while the secondary antibody was diluted 5000-fold. Chemi Lumi ONE Ultra (Nicolai tissue, 11644-40) was used for detection. The detected band strength was analyzed with a lumino image analyzer LAS-4000 mini (Fuji Film) and ImageQuant™ software (GE Healthcare).

(Results)

(mTOR siRNA Suppresses Production of Fibronectin Induced by Recombinant Human TGF-β2)

Figure 9:
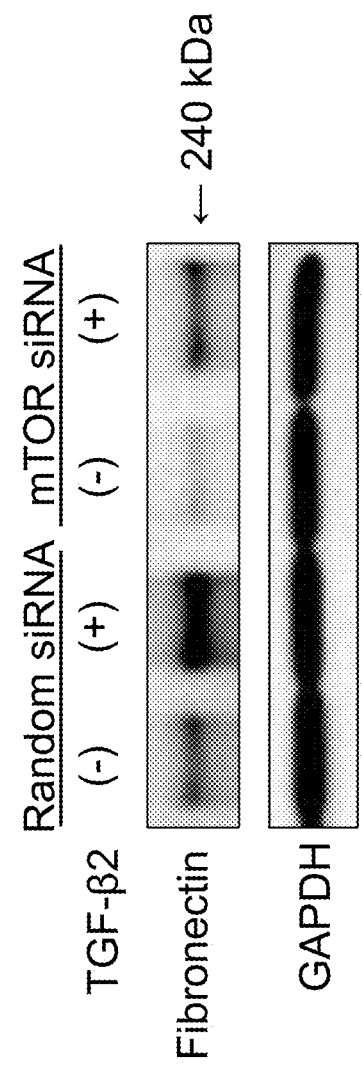
FIG. 9 shows the results of western blot on fibronectin and GAPDH. The figure, from the left, shows a Random siRNA-supplemented group, a TGF-β2+Random siRNA-supplemented group, an mTOR siRNA-supplemented group, and a TGF-β2+mTOR siRNA-supplemented group.

The results are shown in FIG. 9. When iFECDs were stimulated with Recombinant Human TGF-β2 without using mTOR siRNA, production of fibronectin was observed in iFECD. On the other hand, production of fibronectin was hardly observed in the mTOR siRNA supplemented group. Thus, expression of fibronectin was found to be suppressed by western blot analysis in mTOR siRNA.

Example 10: Suppression Effect of Each mTOR Inhibitor on Caspase Activity Induced by TGF-β2

This Example demonstrated suppression effect of each type of mTOR inhibitor on the caspase activity induced by TGF-β2.

(Materials and Methods)

The medium was removed from a culture dish in which iFECDs were being cultured, and the cells were supplemented with 1×PBS (−) that was preheated to 37° C., and were washed. This was repeated twice. The cells were supplemented again with 1×PBS (−) and incubated for 3 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes.

DMEM (Nacalai Tesque, 08456-36)+10% FBS (Biowest, S1820-500)+1% P/S (Nacalai Tesque, 26252-94) was used as the medium.

Corneal endothelial cells from immortalized FECD patients (lot: iFECD3-5) were seeded on a 96-well plate at a ratio of $4 \times 10^3$ cells per well and cultured for 24 hours at 37° C. (5% $CO_2$) (medium: DMEM+10% FBS+1% P/S). After 24 hours, the medium was removed. Each mTOR inhibitor was added to culture the cells for 24 hours (medium: DMEM+2% FBS+1% P/S). After 24 hours, the medium was removed. Media containing 10 ng/ml of Recombinant Human TGF-β2 (Wako, 200-19911) and each mTOR inhibitor were added to culture the cells for 24 hours (medium: DMEM+2% FBS+1% P/S). After 24 hours, the cell morphology and apoptosis were observed under a phase difference microscope.

After observation, measurement of caspase 3/7 activity by Caspase-Glo® 3/7 Assay was carried out with the following procedure.

The medium was discarded to achieve 50 µl per well. 50 µl/well of Caspase Glo® 3/7 Assay Reagent (mixture of Caspase-Glo® 3/7 Assay Buffer and Caspase-Glo® 3/7 Assay Substrate) (Promega, G8091) solution was added so as to achieve 1:1 with the medium. The operations hereafter were carried out while being shaded. A shaker was used to mix the content well for two minutes at about 120 minutes$^{-1}$ to then be left for 40 minutes at room temperature. After being left, 80 µl was moved to Assay plate (Corning, 3912, Assay plate 96 well, white polystyrene) and absorbance was measured using GloMax-Multi Detection System (Promega, E7051).

The following mTOR inhibitors were used in this Example.

Rapamycin (Wako, #53123-88-9)
Everolimus (Cayman Chemical, #11597)
Temsirolimus (Tocris Bioscience, #5264)
PI-103 (Cayman Chemical, #10009209)
CC-223 (Cayman Chemical, #19917)
INK128 (Cayman Chemical, #11811)
AZD8055 (Cayman Chemical, #16978)
KU 0063794 (Tocris Bioscience, #3725)
(Results)
(Rapamycin)

Figure 10:
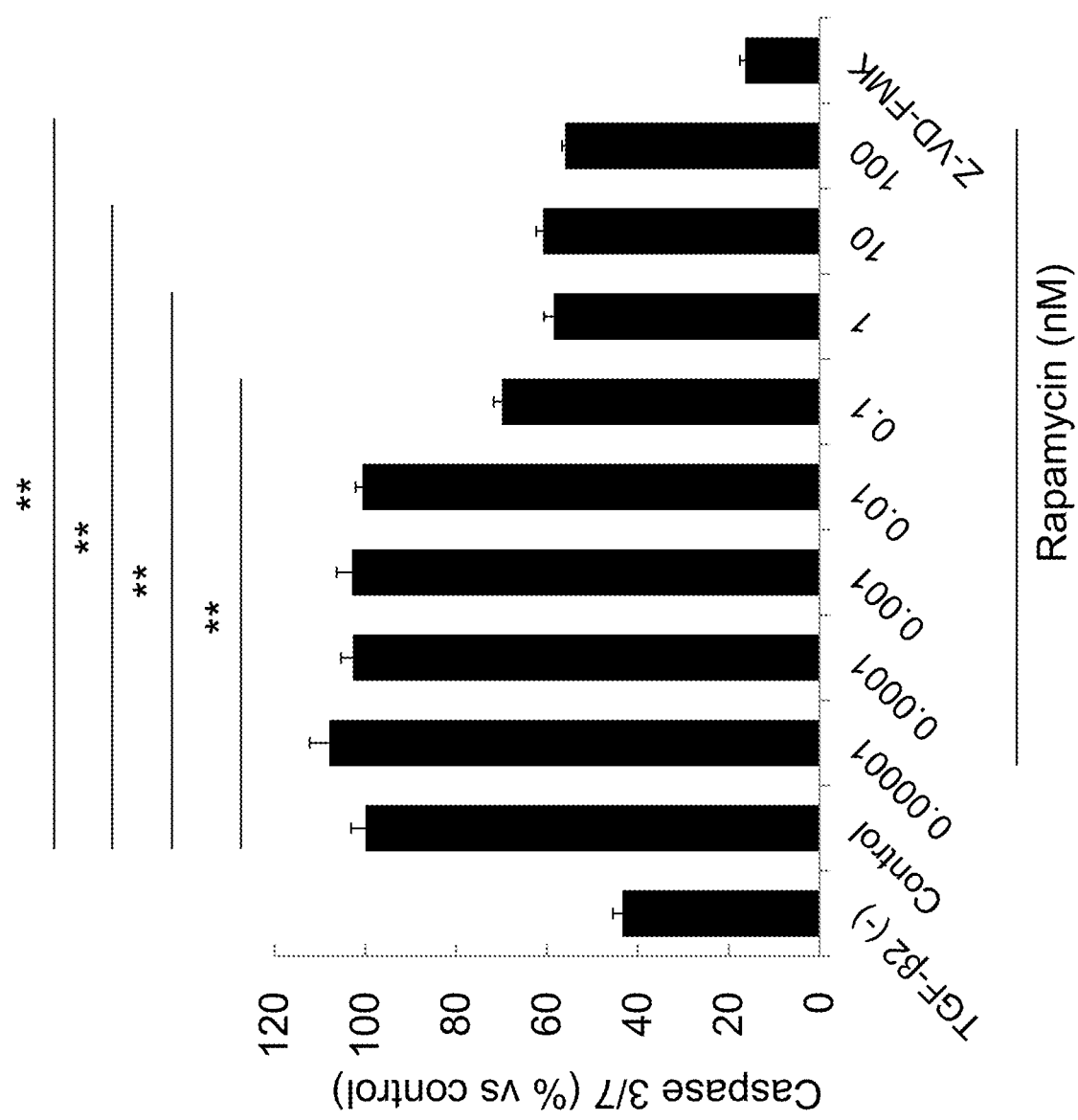
FIG. 10 shows a graph of caspase 3/7 activity. The figure, from the left, shows a TGF-β2-non-supplemented group, a control group, TGF-β2 (10 ng/ml)+rapamycin (0.00001 nM, 0.0001 nM, 0.001 nM, 0.01 nM, 0.1 nM, 1 nM, 10 nM, 100 nM), and TGF-β2 (10 ng/ml)+Z-VD-FMK (10 μM). The statistical significance was tested by the Dunnett-t test (* indicates p<0.05 and ** indicates p<0.01. n=5).

The results are shown in FIG. 10. Caspase-Glo® 3/7 Assay can measure the activity of caspase 3/7 that is involved in apoptosis induction. The higher the activity of caspase 3/7, the more cell damage is induced. From FIG. 10, a significant difference was not found in the activity of caspase 3/7 compared to control when 0.00001, 0.0001, 0.001 and 0.01 nM of rapamycin was supplemented. On the other hand, the activity of caspase 3/7 was found to be significantly suppressed compared to the control group when 0.1, 1, 10 and 100 nM of rapamycin was supplemented. It was revealed that even with a concentration that is extremely low as 0.1 nM, rapamycin significantly suppresses caspase 3/7 activity.

(Everolimus)

Figure 11:
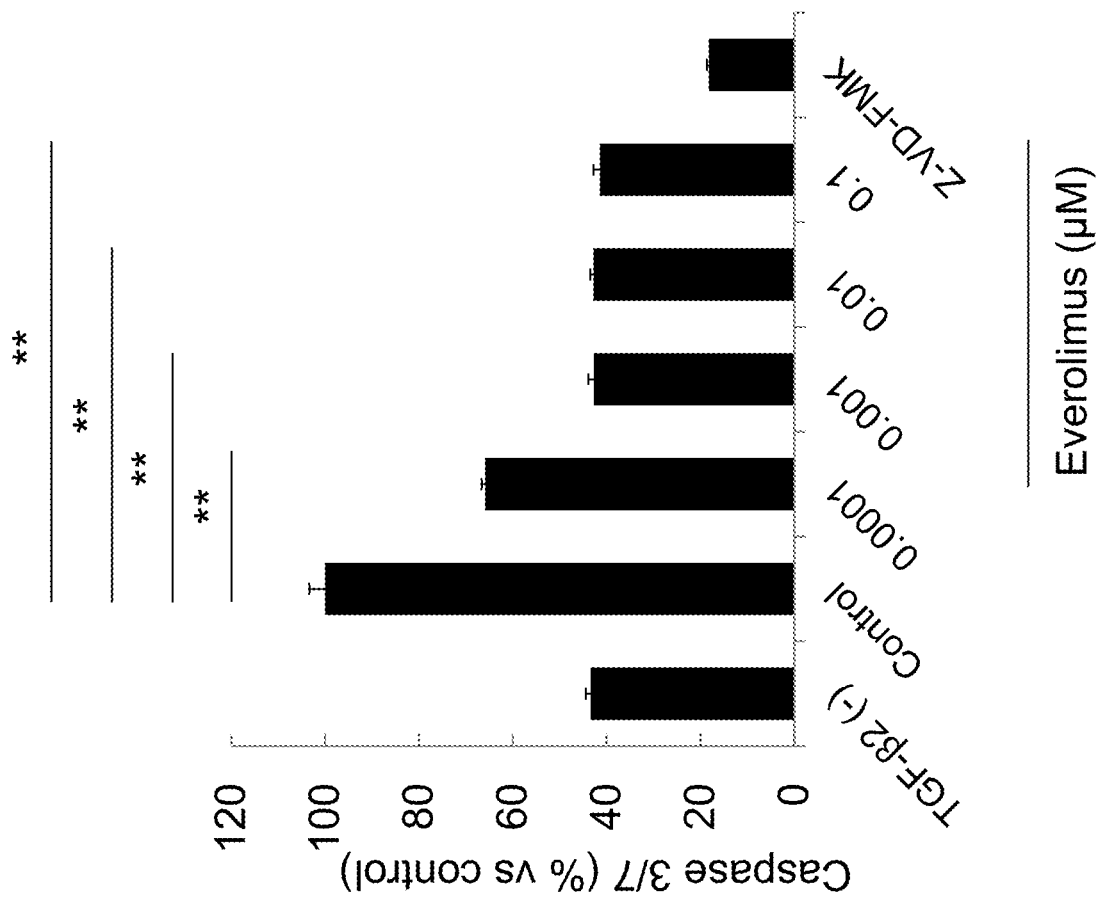
FIG. 11 shows a graph of caspase 3/7 activity. The figure shows, from the left, a TGF-β2-non-supplemented group, a control group, TGF-β2 (10 ng/ml)+everolimus (0.0001 μM, 0.001 μM, 0.01 μM, 0.1 μM), and TGF-β2 (10 ng/ml)+Z-VD-FMK (10 μM). The statistical significance was tested by the Dunnett-t test (* indicates p<0.05 and ** indicates p<0.01. n=5).

The results are shown in FIG. 11. The activity of caspase 3/7 was found to be significantly suppressed compared to the control when 0.0001, 0.001, 0.01 µM and 0.1 µM of everolimus was supplemented. It was revealed that even with a concentration that is extremely low as 0.0001 µM, everolimus significantly suppresses caspase 3/7 activity.

(Temsirolimus)

Figure 12:
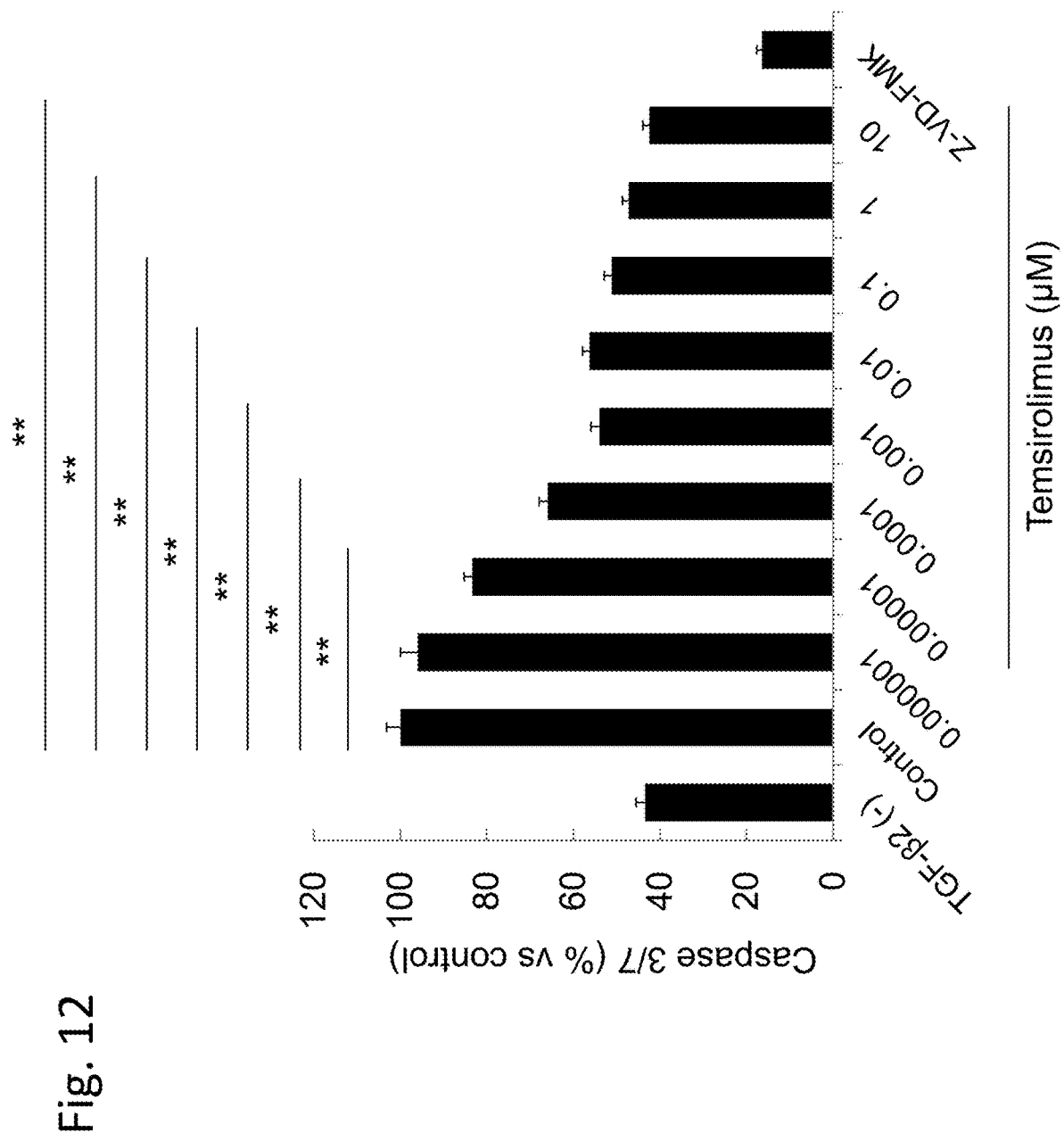
FIG. 12 shows a graph of caspase 3/7 activity. The figure, from the left, shows a TGF-β2-non-supplemented group, a control group, TGF-β2 (10 ng/ml)+temsirolimus (0.000001 μM, 0.00001 μM, 0.0001 μM, 0.001 μM, 0.01 μM, 0.1 μM, 1 μM, 10 μM), and TGF-β2+Z-VD-FMK (10 μM). The statistical significance was tested by the Dunnett-t test (* indicates p<0.05 and ** indicates p<0.01. n=5).

The results are shown in FIG. 12. A significant difference was not found in the activity of caspase 3/7 compared to the control when 0.000001 µM of temsirolimus was supplemented. On the other hand, the activity of caspase 3/7 was found to be significantly suppressed compared to the control when 0.00001, 0.0001, 0.001, 0.01, 0.1, 1 and 10 µM of temsirolimus was supplemented. It was revealed that even with a concentration that is extremely low as 0.00001 µM, everolimus significantly suppresses caspase 3/7 activity.

(PI-103)

Figure 13:
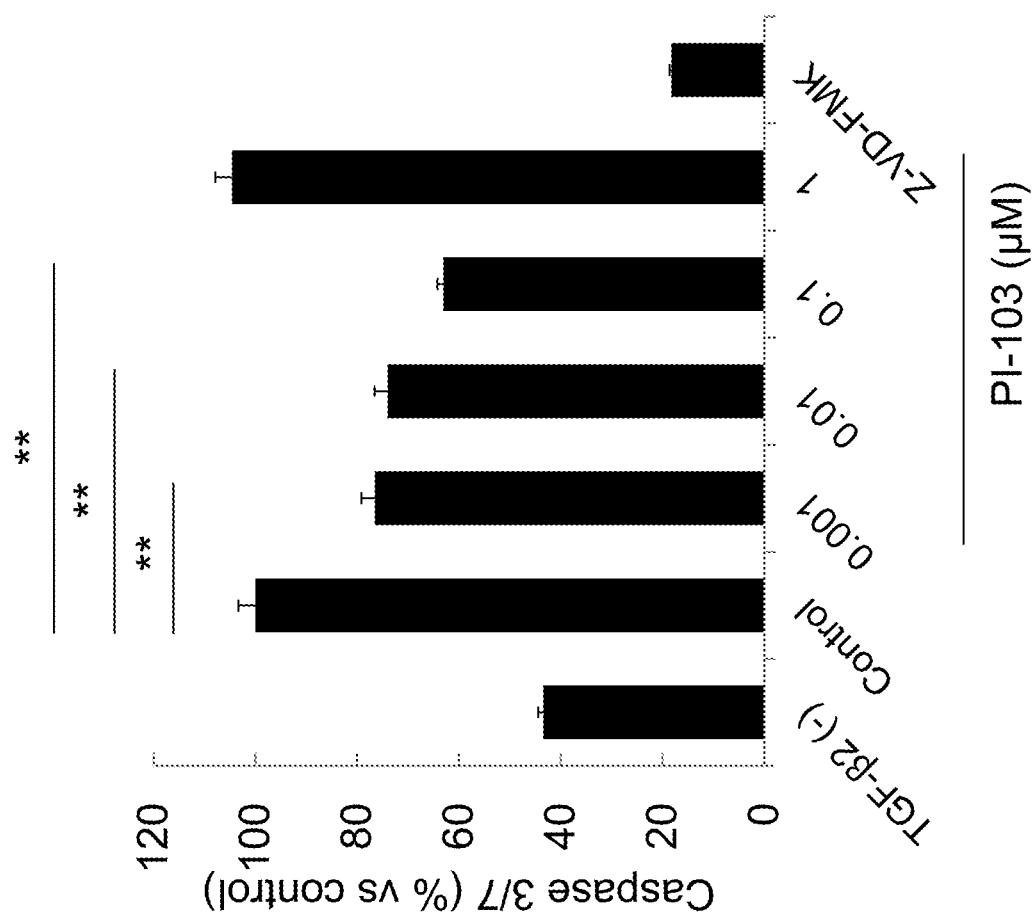
FIG. 13 shows a graph of caspase 3/7 activity. The figure, from the left, shows a TGF-β2-non-supplemented group, a control group, TGF-β2 (10 ng/ml)+Pl-103 (0.001 μM, 0.01 μM, 0.1 μM, 1 μM), and TGF-β2 (10 ng/ml)+Z-VD-FMK (10 μM). The statistical significance was tested by the Dunnett-t test (* indicates p<0.05 and ** indicates p<0.01. n=5).

The results are shown in FIG. 13. A significant difference was not found in the activity of caspase 3/7 compared to the control when 1 µM of PI-103 was supplemented. On the other hand, the activity of caspase 3/7 was found to be significantly suppressed compared to the control when 0.001, 0.01, and 0.1 µM of PI-103 was supplemented.

(CC-223)

Figure 14:
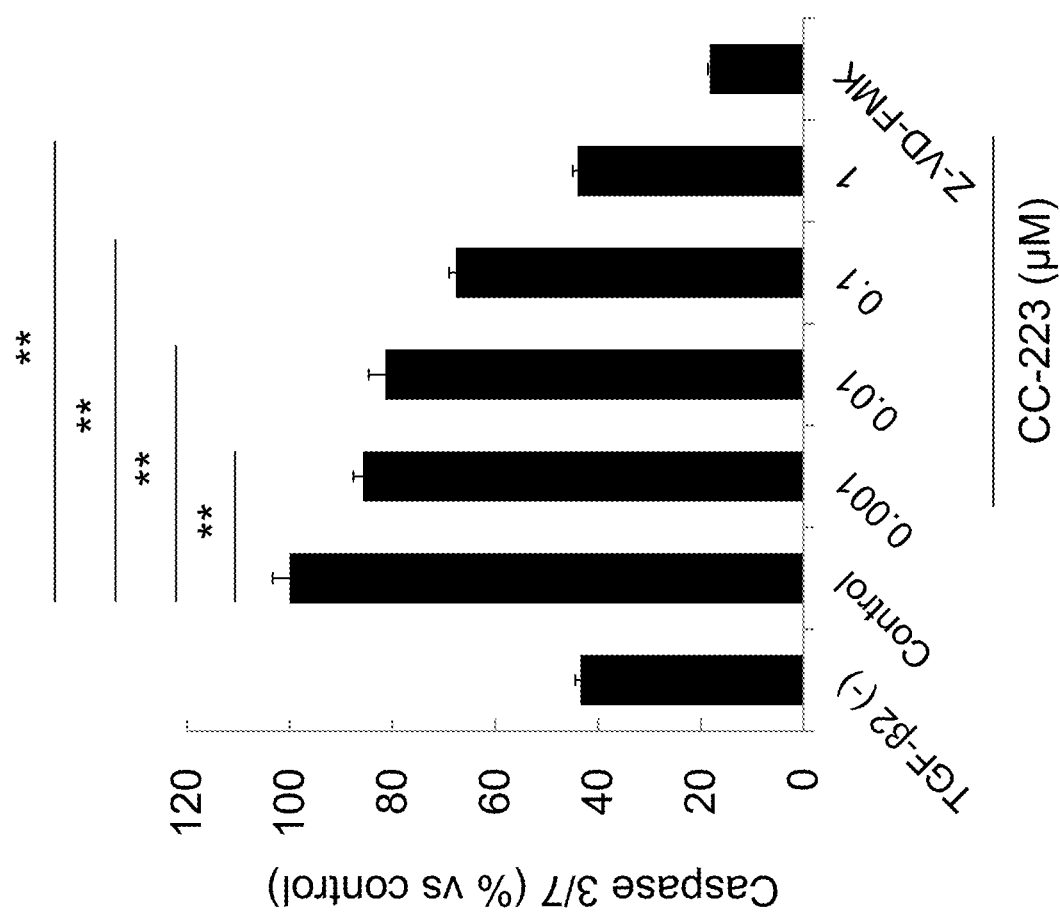
FIG. 14 shows a graph of caspase 3/7 activity. The figure shows, from the left, a TGF-β2-non-supplemented group, a control group, TGF-β2 (10 ng/ml)+CC-223 (0.001 μM, 0.01 μM, 0.1 μM, 1 μM), and TGF-β2 (10 ng/ml)+Z-VD-FMK (10 μM). The statistical significance was tested by the Dunnett-t test (* indicates p<0.05 and ** indicates p<0.01. n=5).

The results are shown in FIG. 14. The activity of caspase 3/7 was found to be significantly suppressed compared to the control when 0.001, 0.01, 0.1 and 1 µM of CC-223 was supplemented.

(INK128)

Figure 15:
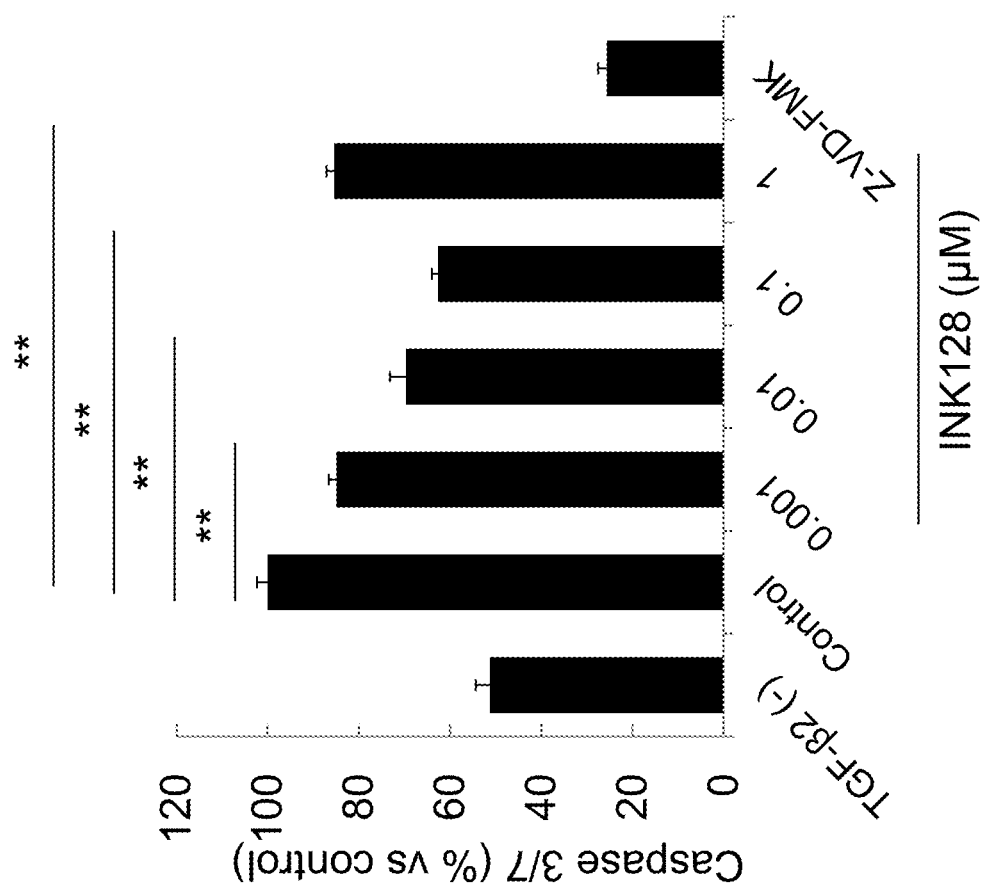
FIG. 15 shows a graph of caspase 3/7 activity. The figure shows, from the left, a TGF-β2-non-supplemented group, a control group, TGF-β2 (10 ng/ml)+INK128 (0.001 μM, 0.01 μM, 0.1 μM, 1 μM), and TGF-β2 (10 ng/ml)+Z-VD-FMK (10 μM). The statistical significance was tested by the Dunnett-t test (* indicates p<0.05 and ** indicates p<0.01. n=5).

The results are shown in FIG. 15. The activity of caspase 3/7 was found to be significantly suppressed compared to the control when 0.001, 0.01, 0.1 and 1 µM of INK128 was supplemented.

(AZD8055)

Figure 16:
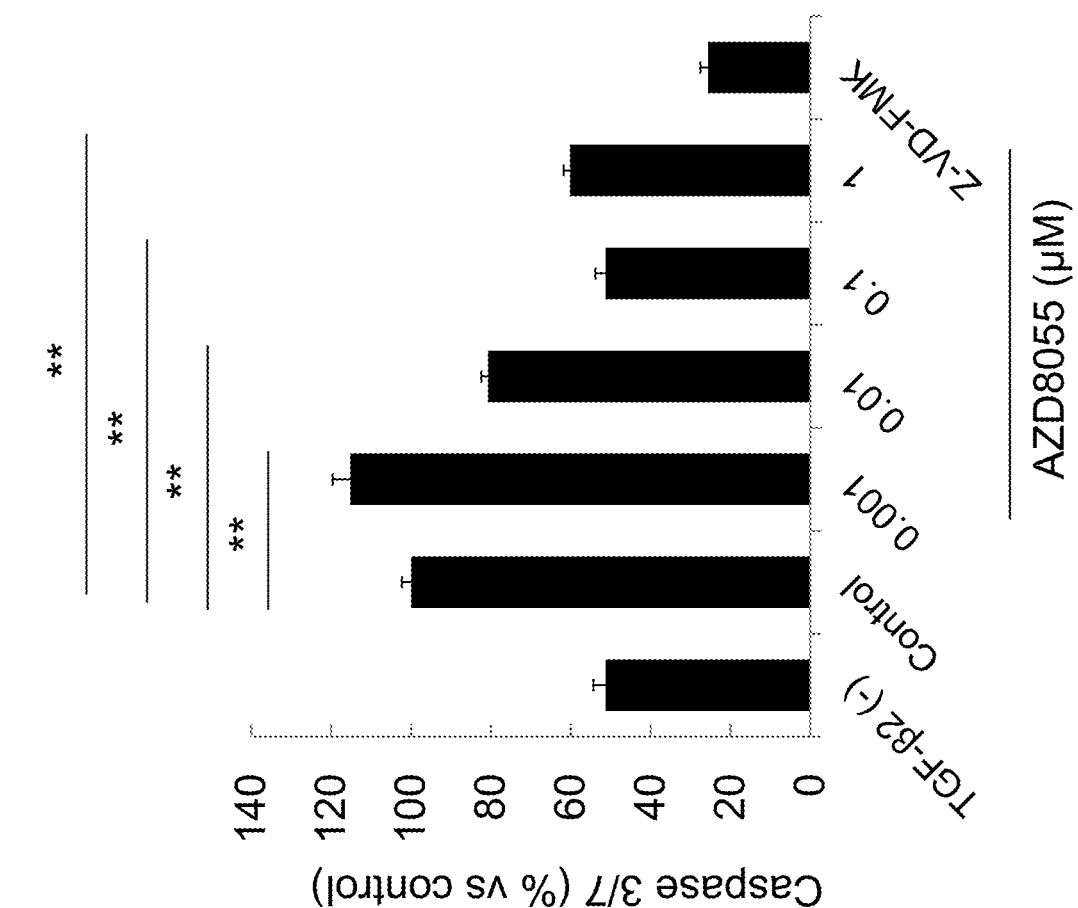
FIG. 16 shows a graph of caspase 3/7 activity. The figure shows, from the left, a TGF-β2-non-supplemented group, a control group, TGF-β2 (10 ng/ml)+AZD8055 (0.001 μM, 0.01 μM, 0.1 μM, 1 μM), and TGF-β (10 ng/ml) 2+Z-VD-FMK (10 μM). The statistical significance was tested by the Dunnett-t test (* indicates p<0.05 and ** indicates p<0.01. n=5).

The results are shown in FIG. 16. The activity of caspase 3/7 was found to be significantly suppressed compared to the control when 0.01, 0.1 and 1 µM of AZD8055 was supplemented.

(KU 0063794)

Figure 17:
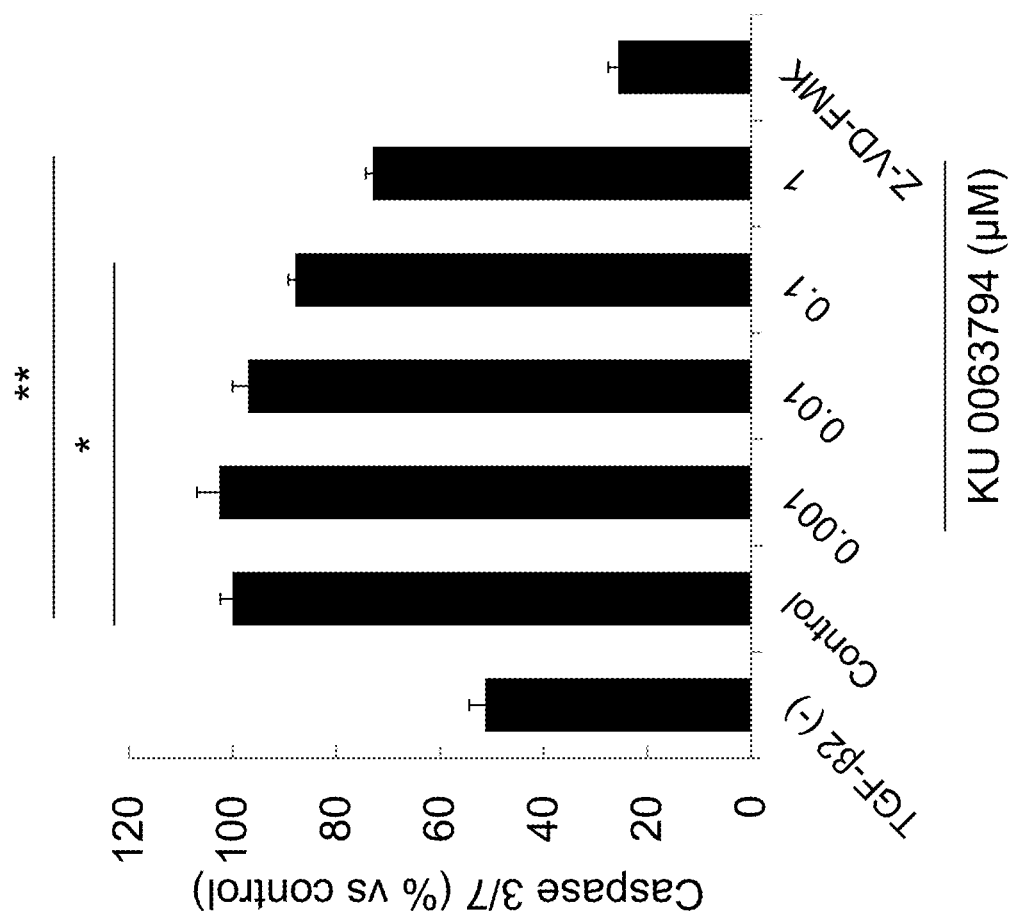
FIG. 17 shows a graph of caspase 3/7 activity. The figure shows, from the left, a TGF-β2-non-supplemented group, a control group, TGF-β2 (10 ng/ml)+KU 0063794 (0.001 μM, 0.01 μM, 0.1 μM, 1 μM), and TGF-β2 (10 ng/ml)+Z-VD-FMK (10 μM). The statistical significance was tested by the Dunnett-t test (* indicates p<0.05 and ** indicates p<0.01. n=5).

The results are shown in FIG. 17. A significant difference was not found in the activity of caspase 3/7 compared to the control when 0.001 and 0.01 µM of KU 0063794 was supplemented. On the other hand, the activity of caspase 3/7 was found to be significantly suppressed compared to the control when 0.1 and 1 µM of KU 0063794 was supplemented.

Example 11: In Vivo Evaluation in a Mouse Model

This Example demonstrated the in vivo effect of an mTOR inhibitor in an evaluation system using a Fuchs' endothelial corneal dystrophy model mouse.

Specifically, this Example instilled an mTOR inhibitor into a mouse having type 8 collagen (Col8a2 Q455K/Q455K), which is a Fuchs' endothelial corneal dystrophy model mouse, to confirm the in vivo effect.

(Materials and Methods)

In vivo evaluation was carried out using Alpha2 Collagen VIII (Col8a2) Q455K knock-in mouse (Hum Mol Genet. 2012 Jan. 15; 21(2): 384-93.), which is a Fuchs' endothelial corneal dystrophy model mouse. Deposition of an extracellular matrix (collagen, fibronectin, or the like) to an endothelial corneal basement membrane (Descemet's membrane) called guttae and cell density reduction due to corneal endothelial damage were found in this model mouse in the same manner as those found in Fuchs' endothelial corneal dystrophy in a human. Thus, this model mouse is understood to be a good model of Fuchs' endothelial corneal dystrophy.

It is possible to treat or prevent outbreak of Fuchs' endothelial corneal dystrophy or delay the progression of the pathology by inhibiting the mTOR pathway of the corneal endothelium by carrying out instillation administration, anterior chamber administration, intravitreal administration, subconjunctival administration, or systemic administration of an mTOR inhibitor, or carrying out gene therapy to such a mouse. Thus, this Example used such a mouse to confirm the effect.

(mTOR Inhibitor Eye Drop Preparation)

25 mg of Torisel® intravenous drip infusion liquid (Pfizer Inc.) (temsirolimus) was used as an eye drop of an mTOR inhibitor. This product and the liquid for dilution attached to this product are mixed in the ratio of 2:3 to prepare 92.78 µl of a 9.7 mM mixture. Furthermore, the 9.7 mM mixture was diluted with 807.22 µl of OTSUKA NORMAL SALINE (Otsuka Pharmaceutical Co., Ltd.) to prepare 900 µl of a 1 mM mixture in a 1.5 ml tube. Next, 900 µl of a 10 µM mixture was prepared using 9 µl of the prepared 1 mM mixture and 891 µl of the OTSUKA NORMAL SALINE. After the preparation, the 1.5 ml tube was covered with aluminum foil to render a shaded state thereto, then be stored in a refrigerator at 4° C.

(Instillation Test on a Mouse)

A mouse having type 8 collagen (Col8a2$^{Q455K/Q455K}$), which is a Fuchs' endothelial corneal dystrophy (FECD) model mouse, was used (obtained from Johns Hopkins University). Severity of FECD was graded from a corneal endothelial image of before the instillation to use FECD model mice that are 20 to 24 weeks old with the same degree of condition. 2 µl of the prepared mTOR inhibitor eye drop (1 mM, 10 µM) was instilled into each of the left and right eyes of 45 mice twice a day in the morning and in the evening. OTSUKA NORMAL SALINE was used for a control. The instillation period was 3 months, during which the person in charge of the experimentation carried out the experimentation in a blinded state regarding the mTOR inhibitor eye drop and the control eye drop (OTSUKA NORMAL SALINE).

(Evaluation of the Effectiveness of the Eye Drop)

Before starting the instillation test, corneal endothelial images were observed with a contact corneal endothelial specular (KSSP slit-scanning wide-field contact specular microscope (Konan medical Inc., Hyogo, Japan)) for grading. After starting the instillation test, the corneal endothelial images of the mice were observed once every 4 weeks with the contact corneal endothelial specular to evaluate the effectiveness of the mTOR inhibitor eye drop.

(Results)

Figure 19:
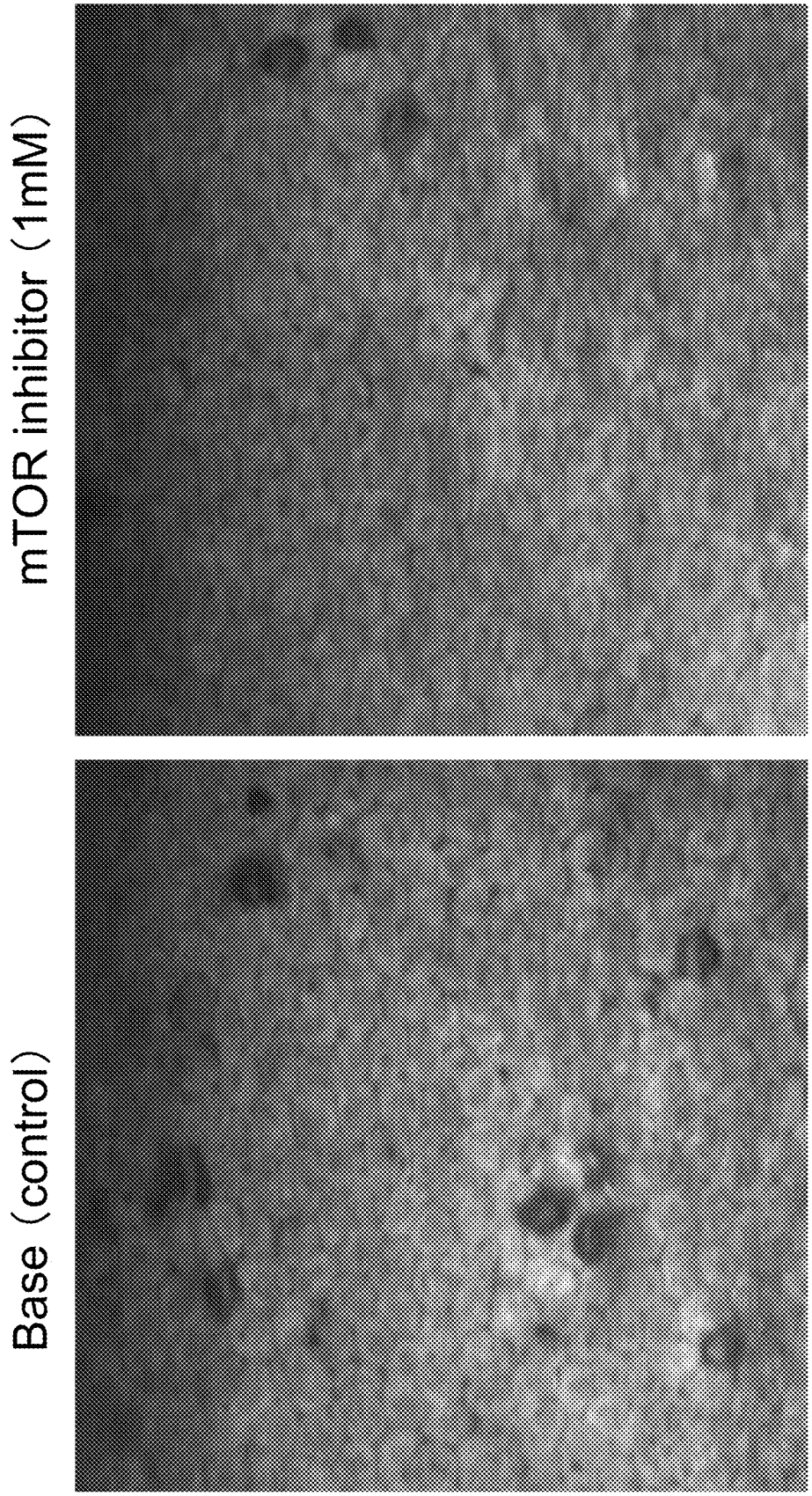
FIG. 19 shows a typical example of a corneal endothelial cell image observed by a contact corneal endothelial specular microscopy using an FECD model mouse, in which 2 μl of mTOR inhibitor eye drop (1 mM) was instilled into each of the left and right eyes twice a day in the morning and in the evening for two months. An image wherein physiological saline (base) was instilled is shown as a control.

FIG. 19 shows a typical example of a corneal endothelial cell image observed by the contact corneal endothelial specular in an FECD model mouse to which 2 µl of the mTOR inhibitor eye drop (1 mM) was instilled into each of the left and right eyes twice a day in the morning and in the evening for 2 months. A corneal endothelial cell image in an FECD model mouse to which a physiological saline solution was instilled is shown as a control. Compared to the control, the size of the corneal endothelial cells are smaller and the cell density is high in an individual into which the mTOR inhibitor eye drop was instilled. Furthermore, generation of a verrucose deposition image of an extracellular matrix called guttae that can be observed in black by the contact corneal endothelial specular was suppressed (FIG. 19).

Figure 20:
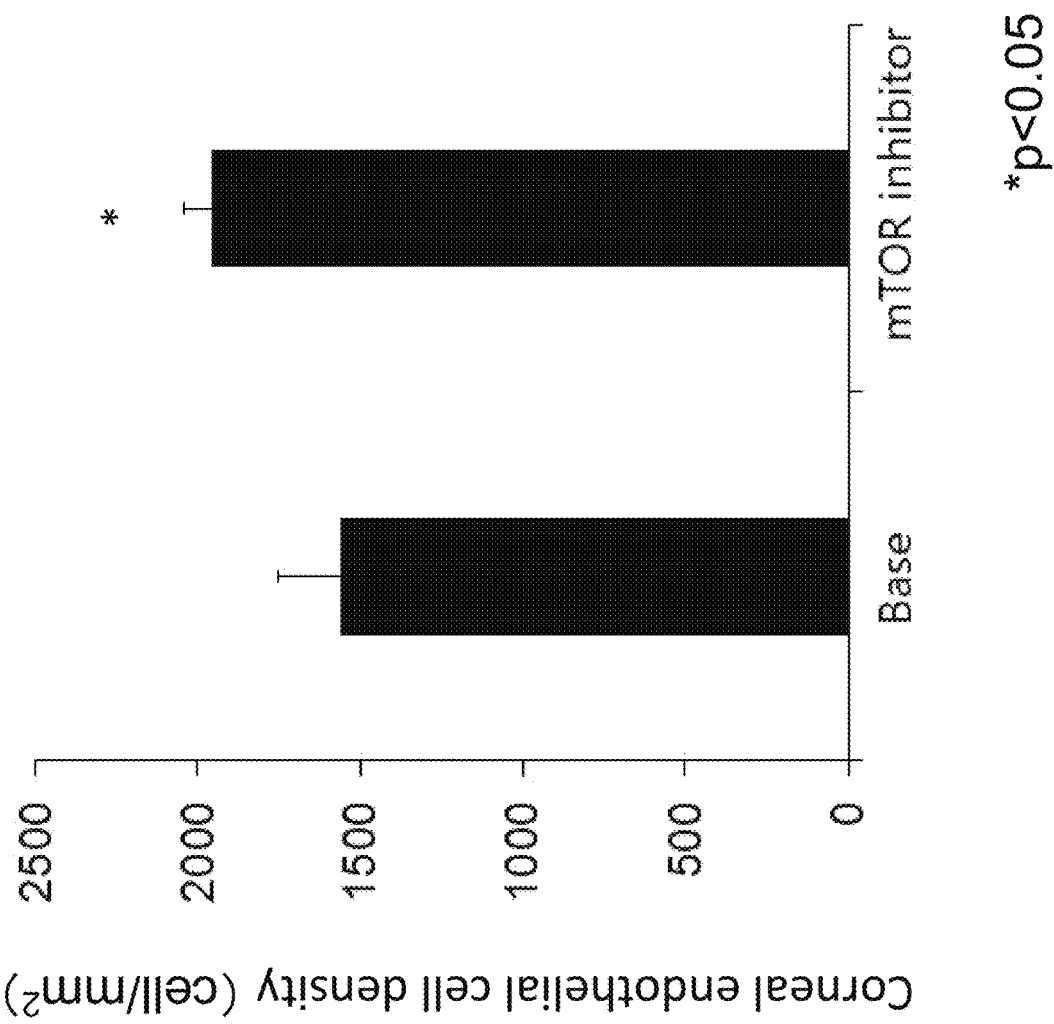
FIG. 20 shows a graph of the corneal endothelial cell density (cell/mm$^2$) in an FECD model mouse, in which an mTOR inhibitor eye drop was instilled. A graph wherein physiological saline (base) was instilled is shown as a control. The statistical significance was tested by the Student's t test (* indicates p<0.05. n=3).

Corneal endothelial cell density of the control was an average of 1558 cells/mm$^2$, whereas the average was 1957 cells/mm$^2$ in the mTOR inhibitor eye drop group, which was significantly higher, thereby suppressing the corneal endothelial cell density reduction found in an FECD model mouse (FIG. 20). This suggests that generation of edema of the corneal stroma, corneal epithelial edema, or the like, which is often found when the corneal endothelial cell density is generally about 1000 cells/mm$^2$ or lower, can be prevented by suppressing corneal endothelial cell reduction by instillation administration of the mTOR inhibitor in an FECD patient.

Figure 21:
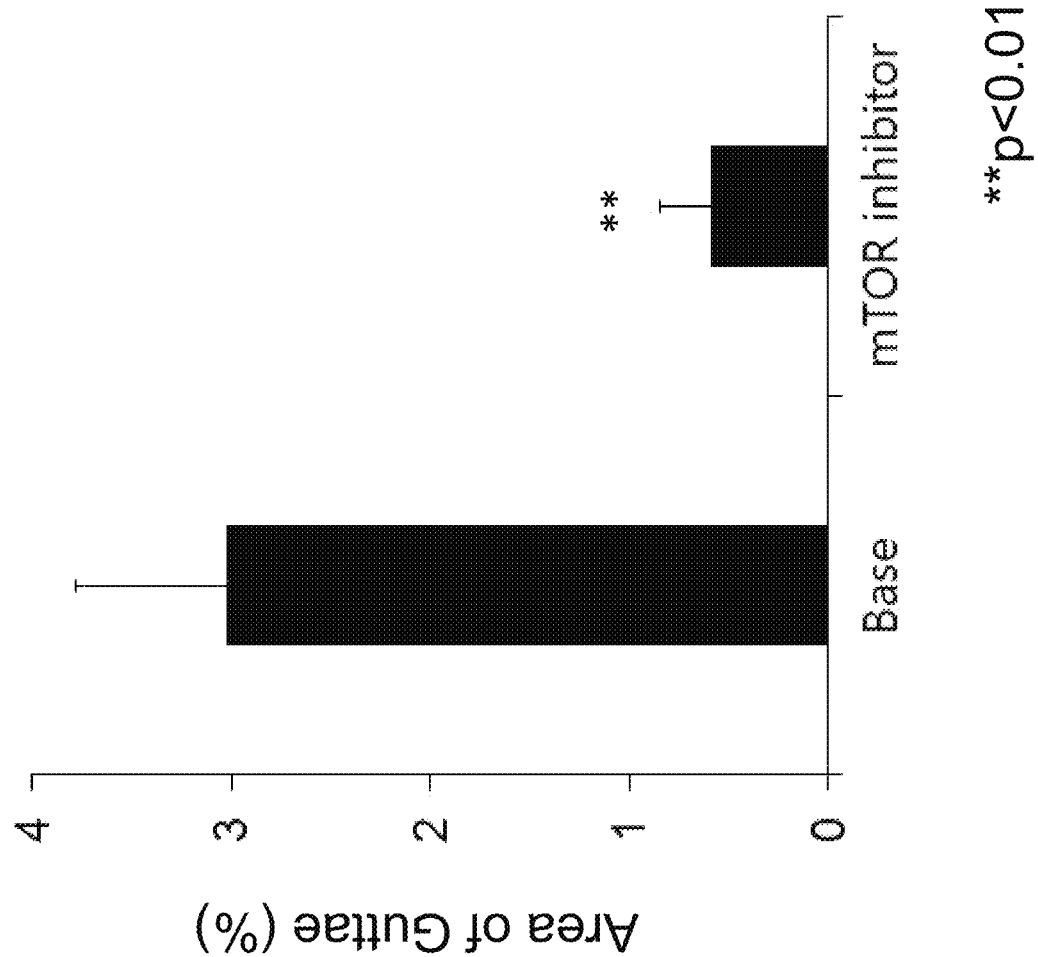
FIG. 21 shows a graph of the area (%) of guttae in an FECD model mouse, in which an mTOR inhibitor eye drop was instilled. A graph wherein physiological saline (base) was instilled is shown as a control. The statistical significance was tested by the Student's t test (** indicates p<0.01. n=3).

In addition, regarding the range of guttae, the control was an average of 3.02%, whereas the mTOR inhibitor instillation group was the average of 0.58%, which was significantly lower, thereby suppressing the generation of guttae found in an FECD model mouse (FIG. 21). When the same analysis was carried out for 15 mice, statistically significant differences were found regarding the Guttae range. Guttae is known to cause decrease of visual function due to irregular reflection of light or the like even in an FECD patient in the early stage who does not have corneal stroma or corneal epithelial edema. Thus, this result suggests that decrease of visual function due to irregular reflection of light can be suppressed by suppressing generation of guttae by instillation administration of an mTOR inhibitor in an FECD patient.

Example 12: Diagnosis and Therapy Example

The present invention is used when diagnosed with Fuchs' endothelial corneal dystrophy or a similar corneal endothelial disease (specific examples thereof include 1) observation of guttae formation, hypertrophy of the Descemet's membrane, corneal epithelial edema, or edema of the corneal stroma by slit-lamp microscopy, 2) observation of images of guttae or corneal endothelial disorder with a specular microscope, 3) observation of corneal edema with a Pentacam, OCT, ultrasonic corneal thickness measuring apparatus, or the like, and 4) when determined as high risk by genetic diagnosis). The present invention can be used in therapy as eye drops, injection into the anterior chamber, administration using controlled-release agent, intravitreal injection, subconjunctival injection, and the like.

A commercially available substance that is compatible with the Japanese Pharmacopoeia, an equivalent product thereof or the like can be used as each component other than the active ingredient.

Example 13: Preparation Example for Eye Drops

As a formulation example, this Example manufactures an eye drop containing an mTOR inhibitor as follows.

The composition of test substances at each concentration is shown below.

| | |
|---|---|
| Rapamycin amount (e.g., final concentration 0.1 mM) | Effective |
| Sodium chloride | 0.85 g |
| Sodium dihydrogen phosphate dehydrate | 0.1 g |
| (Optionally) Benzalkonium chloride | 0.005 g |
| Sodium hydroxide | Optimal dose |
| Purified water | Optimal dose |
| Total amount | 100 mL (pH 7.0) |

The concentration may be diluted using a base consisting of the following components.

| | |
|---|---|
| Sodium chloride | 0.85 g |
| Sodium dihydrogen phosphate dehydrate | 0.1 g |
| (Optionally) Benzalkonium chloride | 0.005 g |
| Sodium hydroxide | Optimal dose |
| Purified water | Optimal dose |
| Total amount | 100 mL (pH 7.0) |

Example 14: Instillation Test on a Mouse

Instillation of an mTOR inhibitor was carried out to a mouse having type 8 collagen (Col8a2 Q455K/Q455K), which is a Fuchs' endothelial corneal dystrophy model mouse, in this Example. This model mouse shows deposition of an extracellular matrix (collagen, fibronectin, or the like), which is recognized in Fuchs' endothelial corneal dystrophy.

(Materials and Methods)

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application 2017-118619 (filed on Jun. 16, 2017). The entire content thereof is incorporated herein by reference.

INDUSTRIAL APPLICABILITY

The present invention provides a medicament for use in treating or preventing a corneal endothelial disorder due to transforming growth factor-β (TGF-β), and/or overexpression of extracellular matrix in corneal endothelial cells, especially a medicament for use in treating or preventing a corneal endothelial disorder in Fuchs' endothelial corneal dystrophy. The present invention provides a technique available to industries (pharmaceutical or the like) involved in techniques associated with formulation or the like based on such a technique.

[Sequence Listing Free Text]
SEQ ID NO: 1: Sense strand of mTOR siRNA
SEQ ID NO: 2: Antisense strand of mTOR siRNA consisting of Fuchs' endothelial corneal dystrophy, post-corneal transplant disorder, corneal endotheliitis, trauma, ophthalmic surgery, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

3. The method of claim 1, wherein the corneal endothelial condition, disorder, or disease is due to overexpression of extracellular matrix (ECM).

4. The method of claim 3, wherein the corneal endothelial condition, disorder, or disease is selected from the group consisting of Fuchs' endothelial corneal dystrophy, guttae formation, hypertrophy of a Descemet's membrane, hypertrophy of a cornea, turbidity, scar, corneal nebula, corneal macula, leucoma, photophobia, and blurred vision.

5. The method of claim 1, wherein the condition, disorder, or disease comprises Fuchs' endothelial corneal dystrophy.

6. The method of claim 1, wherein the mTOR inhibitor is selected from the group consisting of rapamycin, temsirolimus, everolimus, PI-103, CC-223, INK128, AZD8055, KU 0063794, Voxtalisib, Ridaforolimus, NVP-BEZ235, CZ415, Torkinib, Torin 1, Omipalisib, OSI-027, PF-04691502, Apitolisib, WYE-354, Vistusertib, Torin 2, Tacrolimus, GSK1059615, Gedatolisib, WYE-125132, BGT226, Palomid 529, PP121, WYE-687, CH5132799, WAY-600, ETP-46464, GDC-0349, XL388, Zotarolimus, and Chrysophanic Acid.

7. The method of claim 1, wherein the mTOR inhibitor is selected from the group consisting of rapamycin, temsirolimus, and everolimus.

8. The method of claim 1, wherein the mTOR inhibitor is administered as an eye drop.

The invention claimed is:

1. A method for preventing or treating an eye condition, disorder, or disease in a subject, wherein the method comprises administering an effective amount of an mTOR inhibitor to the subject, wherein the eye condition, disorder, or disease is a corneal endothelial condition, disorder, or disease due to a transforming growth factor-β (TGF-β).

2. The method of claim 1, wherein the corneal endothelial condition, disorder, or disease is selected from the group 9. The method of claim 1, wherein the mTOR inhibitor is rapamycin and is administered as an eye drop at least about 0.1 nM.

10. The method of claim 1, wherein the mTOR inhibitor is administered as an eye drop, wherein the mTOR inhibitor is rapamycin and is present in the eye drop at least about 0.1 mM.

11. The method of claim 1, wherein the mTOR inhibitor is temsirolimus and is administered as an eye drop at least about 0.01 nM.

12. The method of claim 1, wherein the mTOR inhibitor is administered as an eye drop, wherein the mTOR inhibitor is temsirolimus and is present in the eye drop at least about 0.01 mM.

13. The method of claim 1, wherein the mTOR inhibitor is everolimus and is administered as an eye drop at least about 0.1 nM.

14. The method of claim 1, wherein the mTOR inhibitor is administered as an eye drop, wherein the mTOR inhibitor is everolimus and is present in the eye drop at least about 0.1 mM.

15. A method for preventing or treating an eye condition, disorder, or disease in a subject, wherein the method consists essentially of administering an effective amount of an mTOR inhibitor to the subject, wherein the eye condition, disorder, or disease is a corneal endothelial condition, disorder, or disease due to a transforming growth factor-β (TGF-β).

16. The method of claim 15, wherein the mTOR inhibitor is rapamycin.

* * * * *